US009504384B2

(12) United States Patent
Toda

(10) Patent No.: US 9,504,384 B2
(45) Date of Patent: Nov. 29, 2016

(54) INFORMATION PROCESSING APPARATUS AND INFORMATION PROCESSING METHOD

(71) Applicant: Sony Corporation, Tokyo (JP)

(72) Inventor: Atsushi Toda, Kanagawa (JP)

(73) Assignee: Sony Corporation, Tokyo (JP)

( * ) Notice: Subject to any disclaimer, the term of this patent is extended or adjusted under 35 U.S.C. 154(b) by 147 days.

(21) Appl. No.: 14/591,539

(22) Filed: Jan. 7, 2015

(65) Prior Publication Data

US 2015/0196199 A1 Jul. 16, 2015

(30) Foreign Application Priority Data

Jan. 14, 2014 (JP) .................. 2014-004259

(51) Int. Cl.
| | | |
|---|---|---|
| *A61B 3/10* | (2006.01) | |
| *A61B 3/12* | (2006.01) | |
| *A61B 3/00* | (2006.01) | |
| *A61B 3/14* | (2006.01) | |
| *A61B 3/113* | (2006.01) | |

(52) U.S. Cl.
CPC ........... *A61B 3/1216* (2013.01); *A61B 3/0008* (2013.01); *A61B 3/113* (2013.01); *A61B 3/14* (2013.01)

(58) Field of Classification Search
CPC ........ A61B 3/103; A61B 3/102; A61B 3/14; A61B 3/12; A61B 3/107; A61B 3/1035; A61B 3/1173; A61B 3/1005
USPC .......................... 351/221, 246; 356/127, 124
See application file for complete search history.

(56) References Cited

U.S. PATENT DOCUMENTS

2010/0290698 A1 11/2010 Freedman et al.
2016/0120402 A1* 5/2016 Limon ................... A61B 3/032
351/241

FOREIGN PATENT DOCUMENTS

| JP | S60-257302 | 12/1985 |
|---|---|---|
| JP | 62-291509 A | 12/1987 |
| JP | H03-128409 | 5/1991 |
| JP | H05-060528 | 3/1993 |
| JP | H05-205030 | 8/1993 |
| JP | H11-113885 | 4/1999 |
| JP | 2006-005003 | 1/2006 |
| JP | 2006-153622 | 6/2006 |
| JP | 2009-300236 | 12/2009 |
| JP | 2010-061768 | 3/2010 |
| JP | 2010-276716 | 12/2010 |
| JP | 2012-194185 A | 10/2012 |

OTHER PUBLICATIONS

Official Action (no English translation available) for Japanese Patent Application No. 2014-004259 mailed May 26, 2016, 8 pages.

* cited by examiner

*Primary Examiner* — Hung Dang
(74) *Attorney, Agent, or Firm* — Sheridan Ross P.C.

(57) ABSTRACT

An information processing apparatus includes: a light emitting unit configured to emit light; an optical unit configured to induce an optical influence to the light from the light emitting unit, the optical unit having an astigmatic lens configured to generate astigmatism with a plurality of focal lengths; a detecting unit configured to detect the light emitted in the light emitting unit, radiated outside through the optical unit, and reflected by an object; and a measuring unit configured to measure a distance to the object based on astigmatism generated in the reflection light detected in the detecting unit.

20 Claims, 36 Drawing Sheets

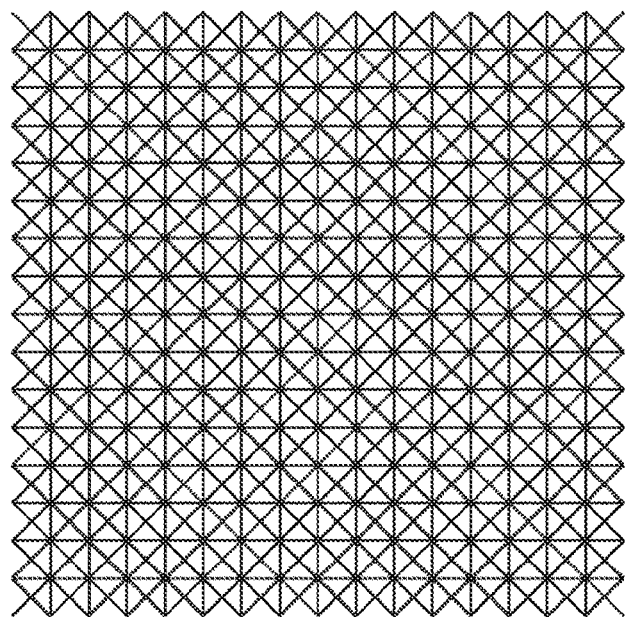
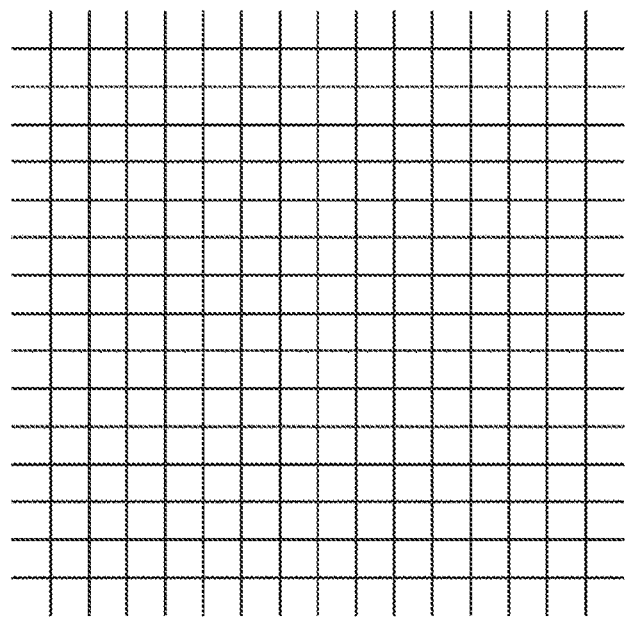
FIG.9

$IR = Bk$
$R^* = R - a_R \times IR$
$G^* = G - a_G \times IR$
$B^* = B - a_B \times IR$ R, G, B; Visible light + IR luminance signal
(measurement value)

R*, G*, B*; Luminance signal of only visible light
(true value)

$a_R$, $a_G$, $a_B$; Coefficient (Constant)

FIG.15

INFORMATION PROCESSING APPARATUS AND INFORMATION PROCESSING METHOD

CROSS REFERENCE TO RELATED APPLICATIONS

This application claims the benefit of priority under 35 U.S.C. §119 from Japanese Priority Patent Application JP 2014-004259 filed Jan. 14, 2014, the entire contents of each which is incorporated herein by reference.

BACKGROUND

The present disclosure relates to an information processing apparatus and an information processing method, and more particularly to an information processing apparatus and an information processing method that can measure a distance more easily.

In the past, a camera system for capturing a depth profile includes a passive method without light radiation and an active method with light radiation. The passive method, having a multi-view type and the like, deteriorates accuracy of a distance measurement under a dark environment or for a low-contrast subject. The active method has a light cut-off method or a time of flight (TOF).

The light cut-off method is a method of measuring a distance to a subject based on an amount of displacement from a reference of a pattern at the time of radiating a certain pattern of light to capture an image (for example, see Japanese Patent Application Laid-open No. SHO 62-291509). Moreover, the TOF is a method of measuring a delay time of light that is reflected back at the speed of light and a distance to a subject based on the delay time (for example, see Japanese Patent Application Laid-open No. 2012-194185).

SUMMARY

However, in the case of the light cut-off method, it is necessary to input the pattern and its position of the reference in a memory and the like in advance. Therefore, this method may increase a cost. Moreover, calculations take more time, so that it may be difficult to perform sufficiently high speed processing.

Moreover, in the case of the TOF, it is necessary to perform measurement processing at a very high speed for measuring the delay time of the reflection light. Accordingly, special techniques are necessary, so that a cost may increase. An example of this measuring method includes an indirect method. In the case of the indirect method, two gates are provided to one pixel of an image sensor. First, one gate reads out a signal, and then the other gate reads out a signal. From the two signal differences, the delay time of returned light is measured. Since the two gates read out, high-speed processing can be achieved. However, two gates or accumulation units are necessary compared to a general complementary metal oxide semiconductor image sensor (CIS), which makes it difficult to decrease a pixel size. Moreover, this method has a complicated circuit configuration, so that a cost may increase.

In view of the circumstances as described above, it is desirable to provide an information processing apparatus that can measure a distance more easily.

According to an embodiment of the present technology, there is provided an information processing apparatus, including: a light emitting unit configured to emit light; an optical unit configured to induce an optical influence to the light from the light emitting unit, the optical unit having an astigmatic lens configured to generate astigmatism with a plurality of focal lengths; a detecting unit configured to detect the light emitted in the light emitting unit, radiated outside through the optical unit, and reflected by an object; and a measuring unit configured to measure a distance to the object based on astigmatism generated in the reflection light detected in the detecting unit.

The measuring unit may be configured to measure the distance to the object based on a change in a radiation shape of the light in the object.

The measuring unit may be configured to measure the distance to the object in accordance with a change in a thickness of each line, in the object, of the light linearly radiated in a plurality of directions.

The optical unit may further include one of a slit, a waveguide, and a diffractive optical element configured to form the radiation shape of the light from the light emitting unit into a cross-shape, and the measuring unit may be configured to measure the distance to the object in accordance with a change in a thickness of each line of the cross-shape in the object.

The optical unit may further include one of a slit, a waveguide, and a diffractive optical element configured to form the radiation shape of the light from the light emitting unit into a radial shape, and the measuring unit may be configured to measure the distance to the object in accordance with a change in a thickness of each line of the radial shape in the object.

The optical unit may further include one of a slit, a waveguide, and a diffractive optical element configured to radiate the light from the light emitting unit to a plurality of positions, and the measuring unit may be configured to measure the distance to the object in accordance with a change in the radiation shape of the light radiated to the plurality of positions of the object.

The optical unit may further include one of a slit, a waveguide, and a diffractive optical element configured to form the radiation shape of the light from the light emitting unit into a stripe shape, and the measuring unit may be configured to measure the distance to the object in accordance with a change in a thickness of each line of the stripe shape in the object.

The astigmatic lens may be a lens configured such that the focal lengths do not change in a radial direction (sagittal) from a central side of the astigmatic lens toward a peripheral side and the focal lengths continuously change in a concentric direction (meridional) centered at one of the center of the astigmatic lens and a vicinity of the center.

The astigmatic lens may be a convertible lens having the focal lengths variable.

The convertible lens may be a lenticular lens.

The astigmatic lens may be constituted of a plurality of lenses.

The measuring unit may be configured to further measure the distance to the object based on displacement of the reflection light detected in the detecting unit and to measure the distance to the object with use of both a measurement result based on the displacement and a distance measurement result based on the astigmatism.

The light emitting unit may be configured to emit infrared light, and the detecting unit may be configured to detect reflection light of the infrared light radiated outside through the optical unit and reflected by the object.

The detecting unit may include an imaging element capable of detecting received visible light and the infrared light and be configured to obtain a captured image made of the visible light with use of the imaging element and detect the reflection light of the infrared light.

The light emitting unit may be configured to emit laser light, and the detecting unit may be configured to detect reflection light of the laser light radiated outside through the optical unit and reflected by the object.

The information processing apparatus may further include: a recognition unit configured to recognize a three-dimensional shape of iris wrinkles of eyeballs of a person serving as the object with use of the distance to the object that is measured by the measuring unit; and an authentication unit configured to authenticate the person based on the three-dimensional shape of the iris wrinkles that is recognized by the recognition unit.

The information processing apparatus may further include: an iris determination unit configured to determine a position and an inclination of an iris of each eyeball and a distance to the eyeball of a person serving as the object with use of the distance to the object that is measured by the measuring unit; a viewpoint determination unit configured to determine a viewpoint of the person based on the position and the inclination of the iris of the eyeball and the distance to the eyeball determined by the iris determination unit; and an information processing unit configured to perform processing in accordance with the viewpoint of the person that is determined by the viewpoint determination unit.

The information processing apparatus may further include: an attitude/movement determination unit configured to determine a position, an attitude and a movement of a person serving as the object with use of the distance to the object that is measured by the measuring unit; and an information processing unit configured to perform processing in accordance with the position, the attitude and the movement of the person that is determined by the attitude/movement determination unit.

The information processing apparatus may further include: an imaging optical unit configured to allow light from a subject to transmit through the imaging optical unit, the imaging optical unit having a variable focal length; an imaging unit configured to photoelectrically convert the light from the subject that is received through the imaging optical unit and obtain image data of the subject; and a focus control unit configured to control the focal length of the imaging optical unit with use of the distance to the object that is measured by the measuring unit.

According to an embodiment of the present technology, there is provided an information processing method, including: emitting light; detecting the light that is radiated outside through an optical unit configured to induce an optical influence to the light and is reflected by an object, the optical unit having an astigmatic lens configured to generate astigmatism with a plurality of focal lengths; and measuring a distance to the object based on the astigmatism generated in the detected reflection light.

In an embodiment of the present technology, light is emitted. The light that is radiated outside through an optical unit configured to induce an optical influence to the light and is reflected by an object is detected, the optical unit having an astigmatic lens configured to generate astigmatism with a plurality of focal lengths.

A distance to the object is measured based on the astigmatism generated in the detected reflection light.

According to an embodiment of the present disclosure, a signal can be processed. In particular, it is possible to measure a distance more easily.

These and other objects, features and advantages of the present disclosure will become more apparent in light of the following detailed description of best mode embodiments thereof, as illustrated in the accompanying drawings.

BRIEF DESCRIPTION OF DRAWINGS

FIG. 9 is a diagram describing an example of a stripe pattern;

FIG. 15 is a diagram showing an example of a color correction calculating method;

DETAILED DESCRIPTION OF EMBODIMENTS

Embodiments for carrying out the present disclosure (hereinafter referred to as embodiments) will be described below. The description will be given in the following order:
1. First embodiment (distance measuring apparatus)
2. Second embodiment (authentication apparatus)
3. Third embodiment (information processing apparatus)
4. Fourth embodiment (information processing apparatus)
5. Fifth embodiment (imaging apparatus)
6. Sixth embodiment (computer)

1. First Embodiment

Distance Measuring Apparatus

Figure 1:
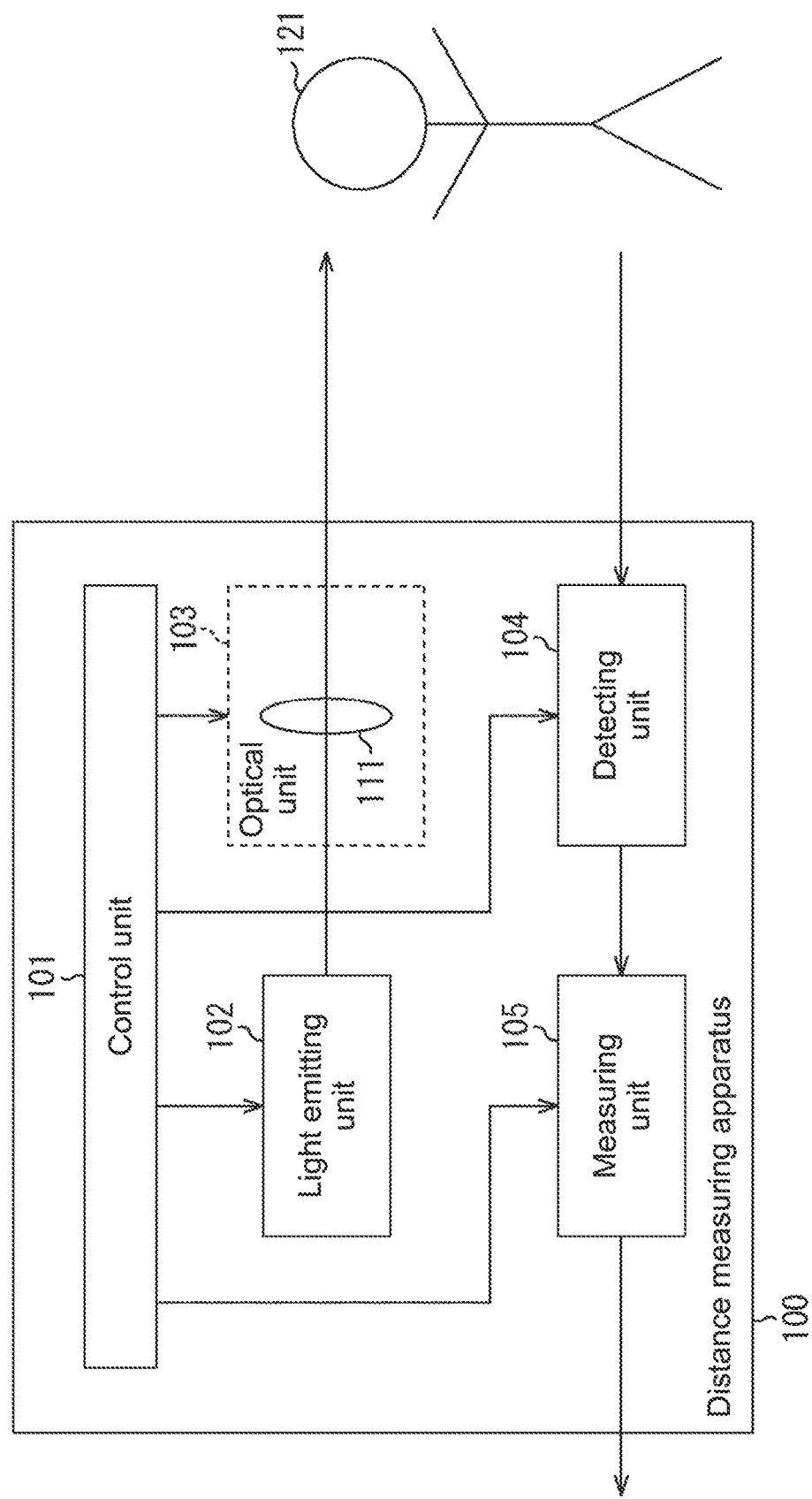
FIG. 1 is a diagram describing a main configuration example of a distance measuring apparatus.

FIG. 1 is a block diagram showing a main configuration example of a distance measuring apparatus according to an embodiment of an information processing apparatus to which the present technology is applied. A distance measuring apparatus 100 shown in FIG. 1 is an apparatus that measures a distance. The distance measuring apparatus 100 radiates light to an object 121 serving as a distance measuring target, detects reflection light reflected by its subject, and measures a distance to the object 121 based on the detection result.

As shown in FIG. 1, the distance measuring apparatus 100 includes a control unit 101, a light emitting unit 102, an optical unit 103, a detecting unit 104, and a measuring unit 105.

The control unit 101 controls respective processing units of the light emitting unit 102 to the measuring unit 105 and executes processing with respect to a distance measurement to the processing units.

The light emitting unit 102 includes an arbitrary light emitter serving as a light source such as an incandescent bulb, a fluorescent bulb, a light emitting diode (LED) and light amplification by stimulated emission of radiation (Laser), and emits light radiated to the object 121. The light emitted from the light emitting unit 102 is discharged outside the distance measuring apparatus 100 through the optical unit 103.

The optical unit 103, made of an arbitrary optical element, induces an optical influence to the light. The configuration of the optical unit 103 may be arbitrary, but includes at least an astigmatic lens 111 configured to allow the light to transmit through from the light emitting unit 102 and cause the transmitted light to generate astigmatism.

The light discharged outside the distance measuring apparatus 100 through the optical unit 103 is radiated to the object 121. The radiation light is reflected by the object 121. The detecting unit 104 detects the reflection light. The detecting unit 104 includes, for example, an image sensor of a charge coupled device (CCD) and a complementary metal oxide semiconductor (CMOS), detects the reflection light reflected by the object 121, and supplies the detection result to the measuring unit 105 as an image data and the like.

Based on the detection result, the measuring unit 105 measures the distance to the object 121. The astigmatism is generated to the reflection light detected in the detecting unit 104 by the astigmatic lens 111. The measuring unit 105 measures a distance between the distance measuring apparatus 100 and the object 121 with use of influence of the astigmatism included in the detection result. The measuring unit 105 outputs the measurement result (information representing the distance to the object 121) outside the distance measuring apparatus 100.

An output method of the measurement result is arbitrary. For example, the output method may be outputted as a digital data from an external output terminal or may be outputted as an image and a video representing a distance from a monitor. Moreover, it is outputted as a voice message representing a distance from a speaker. Further, the distance measurement result may be recorded on a recording medium or may be transmitted to other apparatuses through a communication medium.

Astigmatism

Figure 2:
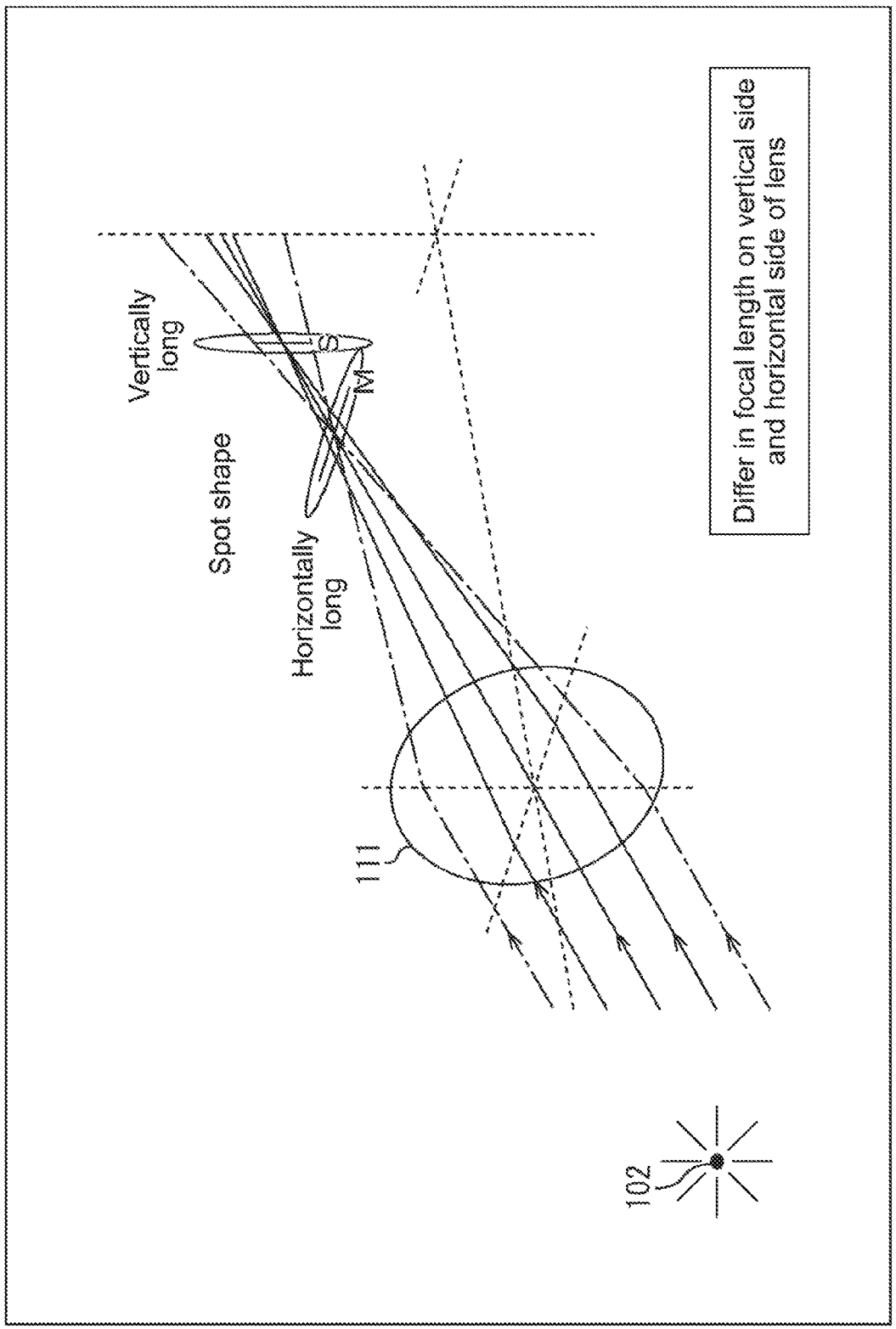
FIG. 2 is a diagram describing an example of a distance measuring method with use of an astigmatic lens.

Next, the astigmatism will be described. The astigmatism is a phenomenon generated when a lens has distortion. For example, as shown in FIG. 2, light (alternate long and short dash line) entered from a vertical direction of the astigmatic lens 111 is focused on a front side thereof, while light (solid line) entered from a horizontal direction of the astigmatic lens 111 is focused on a depth side thereof. That is, in the astigmatic lens 111, refraction of the light is not uniform by the position and a plurality of focal positions are present.

Therefore, for example, when the object 121 is located at a focal position (front side) of the light entered from the vertical direction of the astigmatic lens 111, the light radiated from the light emitting unit 102 is expansively blurred at the position of the object 121 in the horizontal direction. Accordingly, assuming that the light emitting unit 102 is a point light source, a shape of the light radiated to the object 121 (spot shape) is horizontally long.

Moreover, for example, when the object 121 is located at the focal position (depth side) of the light entered from the horizontal direction of the astigmatic lens 111, the light radiated from the light emitting unit 102 is expansively blurred at the position of the object 121 in the vertical direction. Accordingly, assuming that the light emitting unit 102 is the point light source, the shape of the light radiated to the object 121 (spot shape) is vertically long.

That is, by changing the position of the object 121 (distance between the distance measuring apparatus 100 and the object 121), the spot shape is deformed. Therefore, on the contrary, the position of the object 121 (distance between the distance measuring apparatus 100 and the object 121) can be obtained from the spot shape. The measuring unit 105 measures the distance to the object 121 based on a change in the spot shape due to this astigmatism.

Distance Measuring Method

Next, a specific example of the distance measuring method will be described. The measuring method may be any method, as long as it is based on the change in the spot shape due to the astigmatism, but may be obtained as follows, for example.

Figure 3:
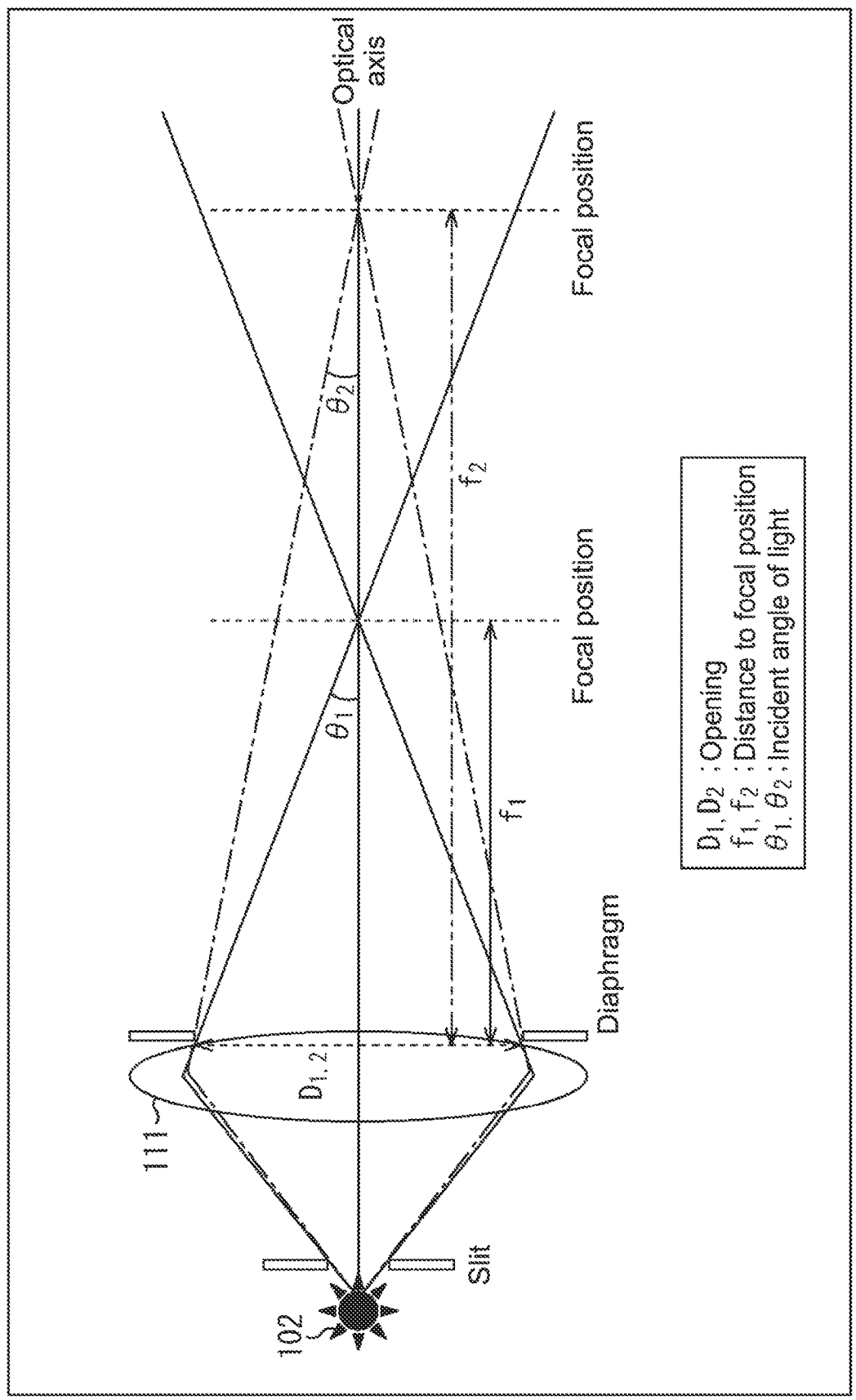
FIG. 3 is a diagram describing an example of the distance measuring method.

For example, as shown in FIG. 3, it is assumed that the light from the light source (light emitting unit 102) is discharged outside the distance measuring apparatus 100 through a slit, the astigmatic lens 111 and a diaphragm of the optical unit 103. Then, as an example shown in FIG. 2, it is assumed that the light entered from the vertical direction of the astigmatic lens 111 is focused on the front side, and the light entered from the horizontal direction of the astigmatic lens 111 is focused on the depth side. It should be noted that in FIG. 3, the light entered from the vertical direction of the astigmatic lens 111 and the light entered from the horizontal direction of the astigmatic lens 111 are also represented in the vertical direction in FIG. 3. As shown in FIG. 3, distances between the diaphragm and each focal position are represented by $f_1$ and $f_2$. Moreover, an opening in the vertical direction of the astigmatic lens 111 is represented by $D_1$ and an opening in the horizontal direction of the astigmatic lens 111 is represented by $D_2$. Further, an angle made by the light passed through an end (vicinity of the diaphragm) in the vertical direction of the astigmatic lens 111 with respect to an optical axis is represented by $\theta_1$, and an angle made by the light passed through an end in the horizontal direction with respect to the optical axis is represented by $\theta_2$. With respect to these angles $\theta_1$ and $\theta_2$, following Equations (1) and (2) are satisfied.

$$\tan \theta_1 = D_1/(2*f_1) \quad (1)$$

$$\tan \theta_2 = D_2/(2*f_2) \quad (2)$$

Figure 4:
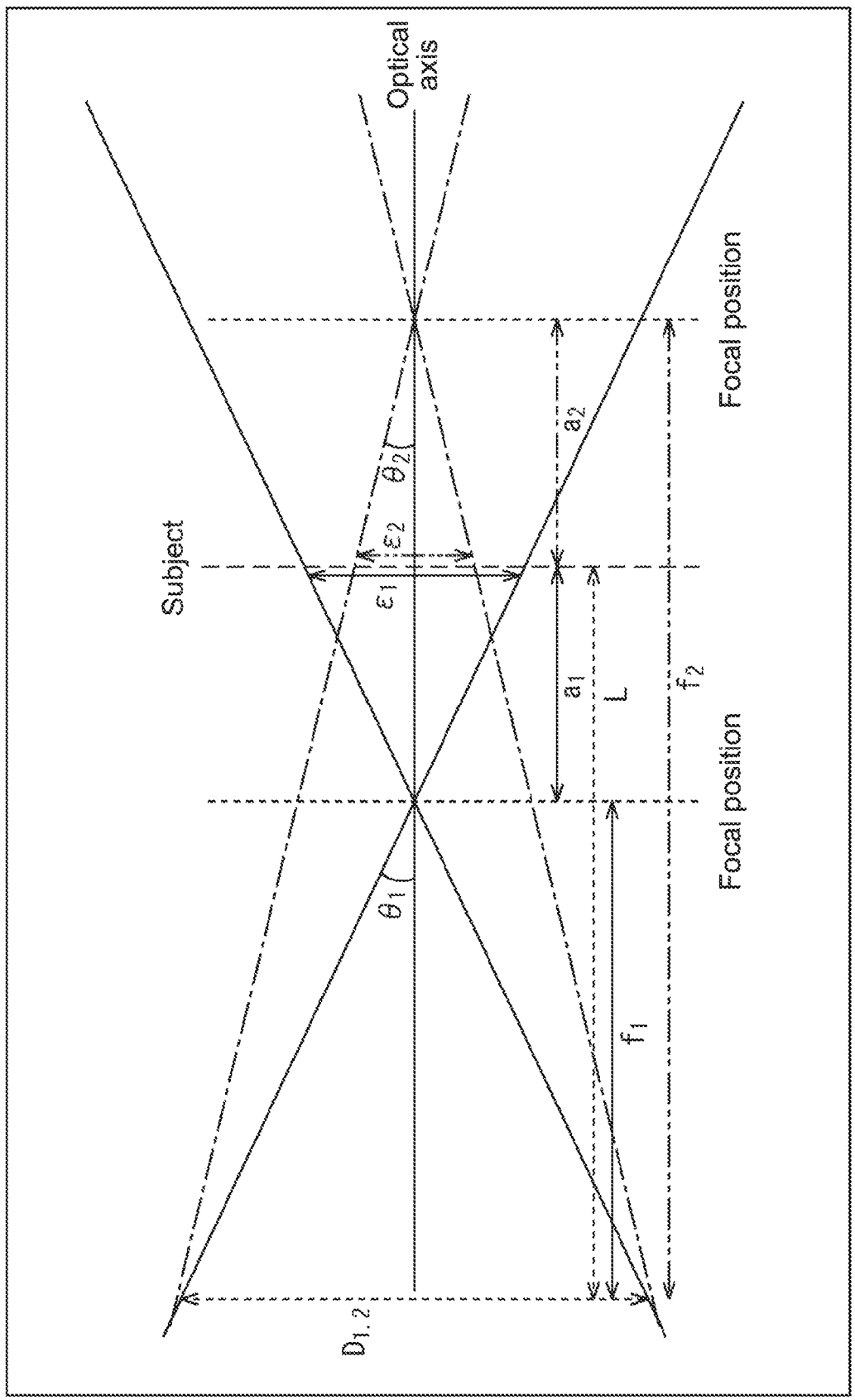
FIG. 4 is a diagram describing an example of the distance measuring method.

FIG. 4 is an enlarged view of the position focused in FIG. 3. In this case, a distance between the diaphragm and the object 121 (subject) is represented by L. In this case, when $a_1$ and $a_2$ are respectively represented by absolute values of differences between L and f1 and L and f2, following Equations (3) and (4) are satisfied.

$$a_1 = |L - f_1| \quad (3)$$

$$a_2 = |f_2 - L| \quad (4)$$

Further, amounts of blurring obtained when the light is radiated to the subject are represented by $\in_1$ and $\in_2$, following Equations (5) and (6) are satisfied.

$$\in_1 = 2*a_1*\tan \theta_1 \quad (5)$$

$$\in_2 = 2*a_2*\tan \theta_2 \quad (6)$$

Values of $D_1$, $D_2$, $f_1$, and $f_2$ are determined by the astigmatic lens 111 and the diaphragm, so that the values can be specifically determined as follows, for example.

$D_2 = 20$ mm
$D_2 = 20$ mm
$f_1 = 50$ mm
$f_2 = 100$ mm

Namely, a relational expression of L and the amounts of blurring $\in_1$ and $\in_2$ can be obtained from Equations (1) to (6) described above. That is, for example, dependency of the amounts of burring $\in_1$ and $\in_2$ to L as shown in a graph of FIG. 5 can be obtained. Therefore, the measuring unit 105 can measure the distance L between the amount (or ratio) of burring in the direction of two astigmatism and the object 121. It should be noted that the amount of blurring becomes ideally zero in the focal position, but in practice, a diffraction limit of the lens prevents the amount of blurring from becoming zero and generally provides some amount of blurring. However, in comparison with the amount of blurring in the case of a non-focused position, the amount of blurring in this focal position is so sufficiently small that it is assumed negligible.

As described above, since the astigmatism is used to measure the distance, the distance measuring apparatus 100 can measure the distance with more ease and high accuracy.

Measurement of Amount of Blurring

Point Light Source

Next, a measuring method of the amount of blurring will be described. The amount of blurring is obtained according to a degree of change a radiation shape (spot shape) of the radiation light in the object 121 detected in the detecting unit 104. The shape of the light radiated to the object 121 is arbitrary.

For example, assuming that the light source which the light emitting unit 102 has is a point light source, substantially uniform parallel light may be discharged to the optical unit 103 from the light emitting unit 102.

When the parallel light from the point light source passes through a lens in which the astigmatism is not generated as the parallel light, the spot shape of the radiation light in the focal position of the lens is ideally formed into a dot. In contrast, when the parallel light from the point light source passes through the astigmatic lens 111, the spot shape is vertically long or horizontally long due to the astigmatism.

Then, the measuring unit 105 may observe the spot shape of the radiation light in the object 121 detected in the detecting unit 104 and obtain the distance to the object 121 based on a degree of change in its shape, that is, a length of a predetermined direction of the spot shape (for example, vertical or horizontal direction). For example, the measuring unit 105 can obtain how close the object 121 is to one of two focal positions (that is, L) by the extent to which the spot shape is vertically long or horizontally long.

The direction for obtaining the length of the spot shape may be any direction, as long as it is a direction of change due to influence of the astigmatism. Namely, the direction for obtaining the length of the spot shape is not limited to the vertical and horizontal directions. For example, it may be directions inclined at angles of 45 degrees and −45 degrees. Moreover, the direction for obtaining the length is not necessarily perpendicular to each other as the example described above.

Figure 5:
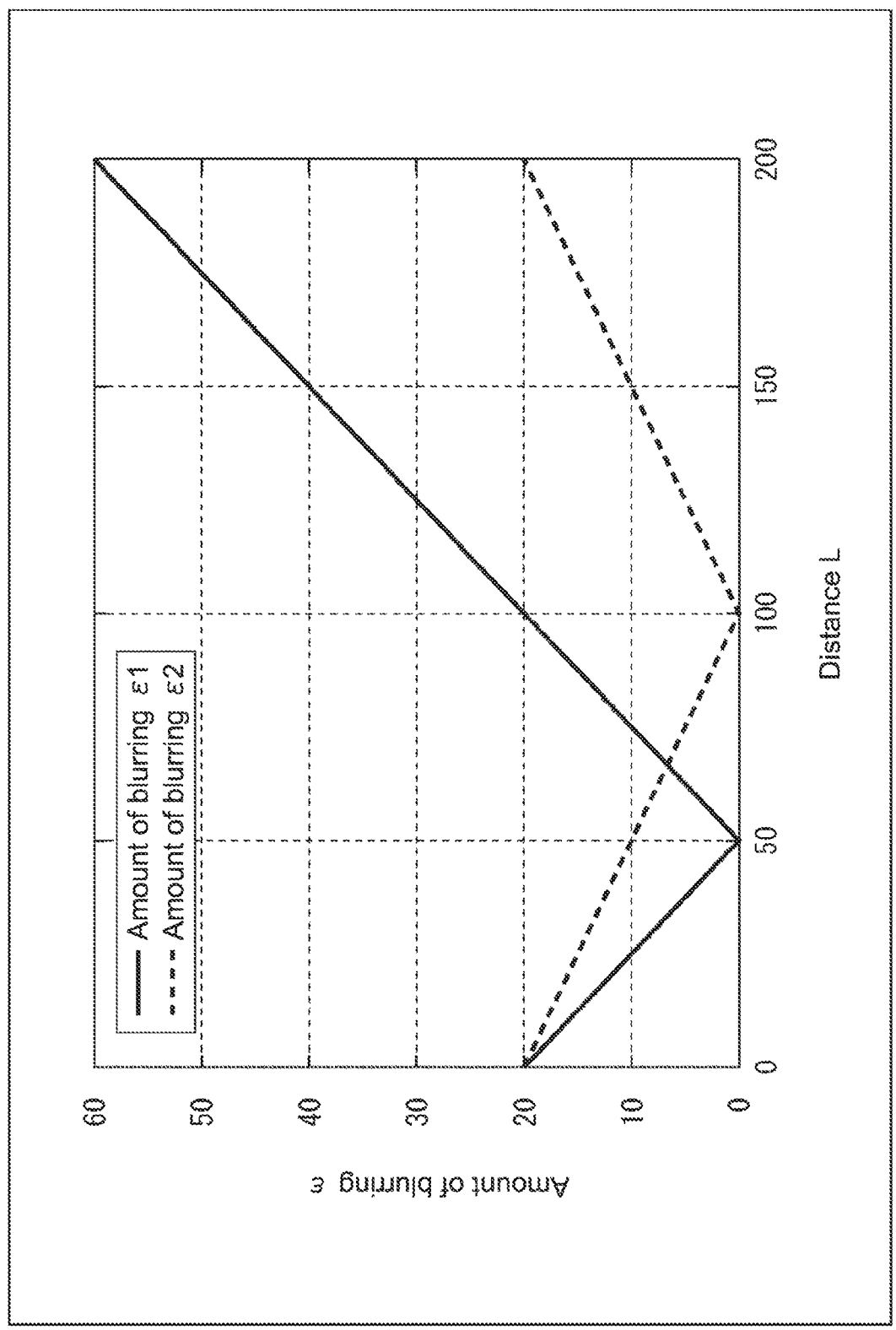
FIG. 5 is a diagram describing an example of the distance measuring method.

The number of the directions for obtaining the length is arbitrary, but a plurality of directions are desirable. This is because it is difficult to decide whether the focal position is located on the front side or the depth side from a length of a single direction as shown in the graph of FIG. 5. Moreover, the distance to the object 121 (position of the object 121) can be obtained more precisely by obtaining the distance to the object 121 from lengths of the plurality of directions (that is, a plurality of focal positions being set as reference).

It should be noted that the point light source which the light emitting unit 102 has can be realized by any method as long as the light source is arranged so that the light passing through the astigmatic lens 111 is allowed to form substantially parallel light. For example, a sufficiently small light source may be used.

Measurement of Amount of Blurring

Cross-Shape

Figure 6:
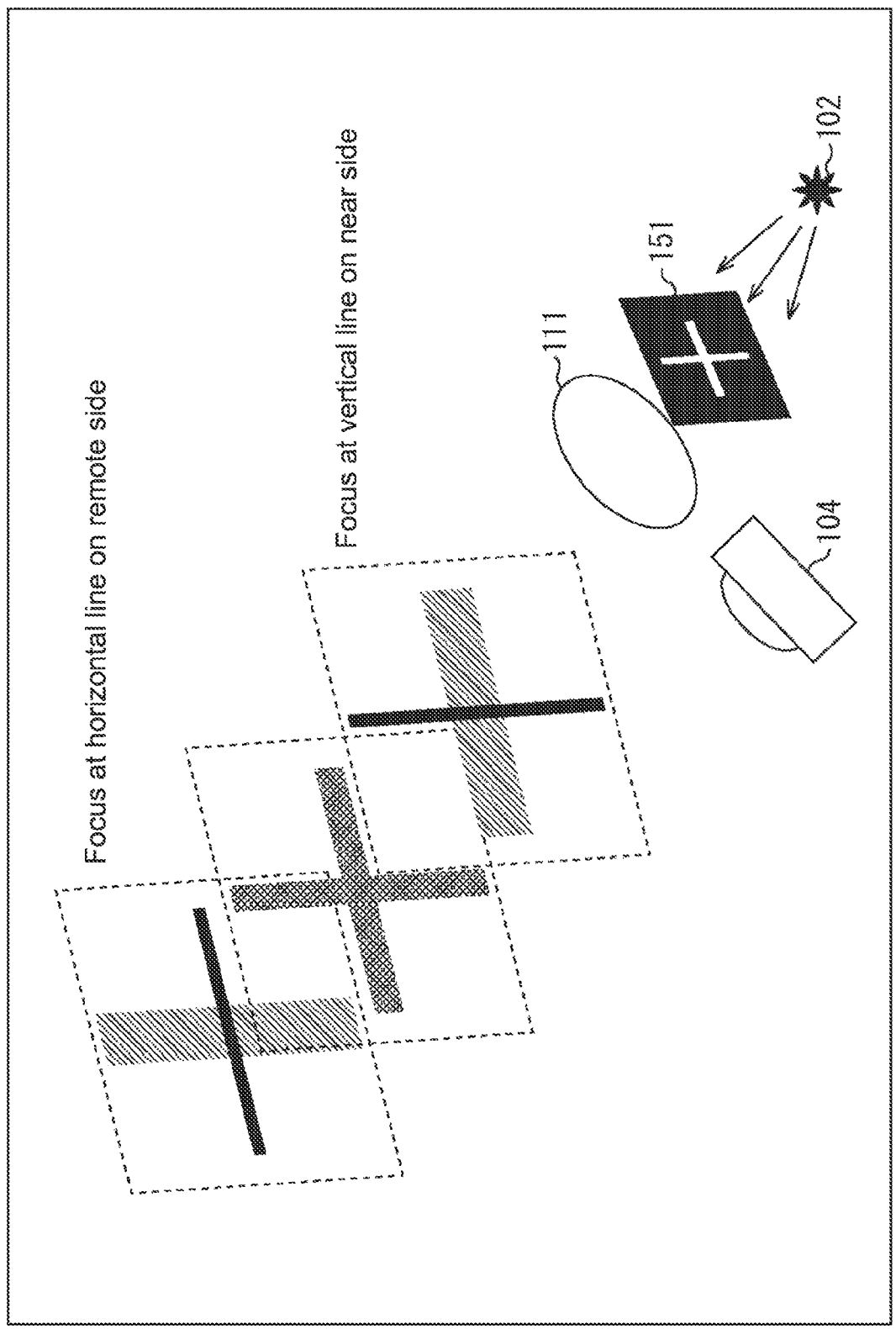
FIG. 6 is a diagram describing an example of a distance measuring method with use of a cross light source.

Moreover, for example, cross-shaped light may radiated to the object 121 from the optical unit 103. A method of realizing such a cross light source is arbitrary, but for example, as shown in FIG. 6, a slit 151 having a cross-shaped opening may be provided between the point light source and the astigmatic lens 111. For example, in the optical unit 103, the cross-shaped slit 151 may be provided on the light emitting unit 102 side of the astigmatic lens 111. Most of light passed through the slit 151 passes through the astigmatic lens 111 while retaining the cross shape and is radiated to the object 121 as described above. Namely, the detecting unit 104 detects a cross-shaped spot shape in the object 121.

When the cross-shaped light passes through the lens in which the astigmatism is not generated, the spot shape of the radiation light in the focal position of the lens has ideally a thin cross-shape. In contrast, when the cross-shaped light passes through the astigmatic lens 111, a thickness of the cross in the spot shape of the radiation light in the focal position of the lens is changed due to the astigmatism.

For example, in FIG. 6, the light is focused in a vertical direction in the vicinity of the focal position on the front side (near side), and the spot shape of the radiation light has a thin cross-shaped vertical line and a thick cross-shaped horizontal line. Moreover, the light is focused in a horizontal direction in the vicinity of the focal position on the depth side (remote side), and the spot shape of the radiation light has a thin cross-shaped horizontal line and a thick cross-shaped vertical line. Further, in the vicinity of a middle point between the focal positions, the spot shape of the radiation light has substantially the same thickness of the cross-shaped horizontal line and the cross-shaped vertical line.

Then, the measuring unit 105 may observe the spot shape of the radiation light in the object 121 detected in the detecting unit 104, obtain how close the object 121 is to one of two focal positions based on a degree of change in its shape, that is, the extent to which the vertical line of the cross-shaped spot shape is thick and the horizontal line of the cross-shaped spot shape is thin, and obtain the distance (L) to the object 121.

It should be noted that the light emitting unit 102 may have the slit 151. Moreover, instead of the slit 151, a light guide plate having a waveguide whose surface shape is formed into a cross shape may be provided. Further, in instead of the slit 151, a diffractive optical element (DOE) may be used to radiate the cross-shaped light. Moreover, the radiation shape (that is, a shape of an opening of the slit 151) is arbitrary and may be other than the cross shape. For example, the radiation shape may be a shape (X-shape) in which directions inclined at angles of 45 degrees and −45 degrees are longitudinal directions. Moreover, the longitudinal directions of the radiation shape (the opening of the slit 151) are not necessarily perpendicular to each other as the example described above.

Further, the number of the longitudinal directions of the radiation shape (the opening of the slit 151) is arbitrary, but a plurality of directions are desirable. This is because it is difficult to decide whether the focal position is located on the front side or the depth side from only a thickness of the length of the single direction as shown in the graph of FIG. 5.

Measurement of Amount of Blurring

Radial Shape

Figure 7:
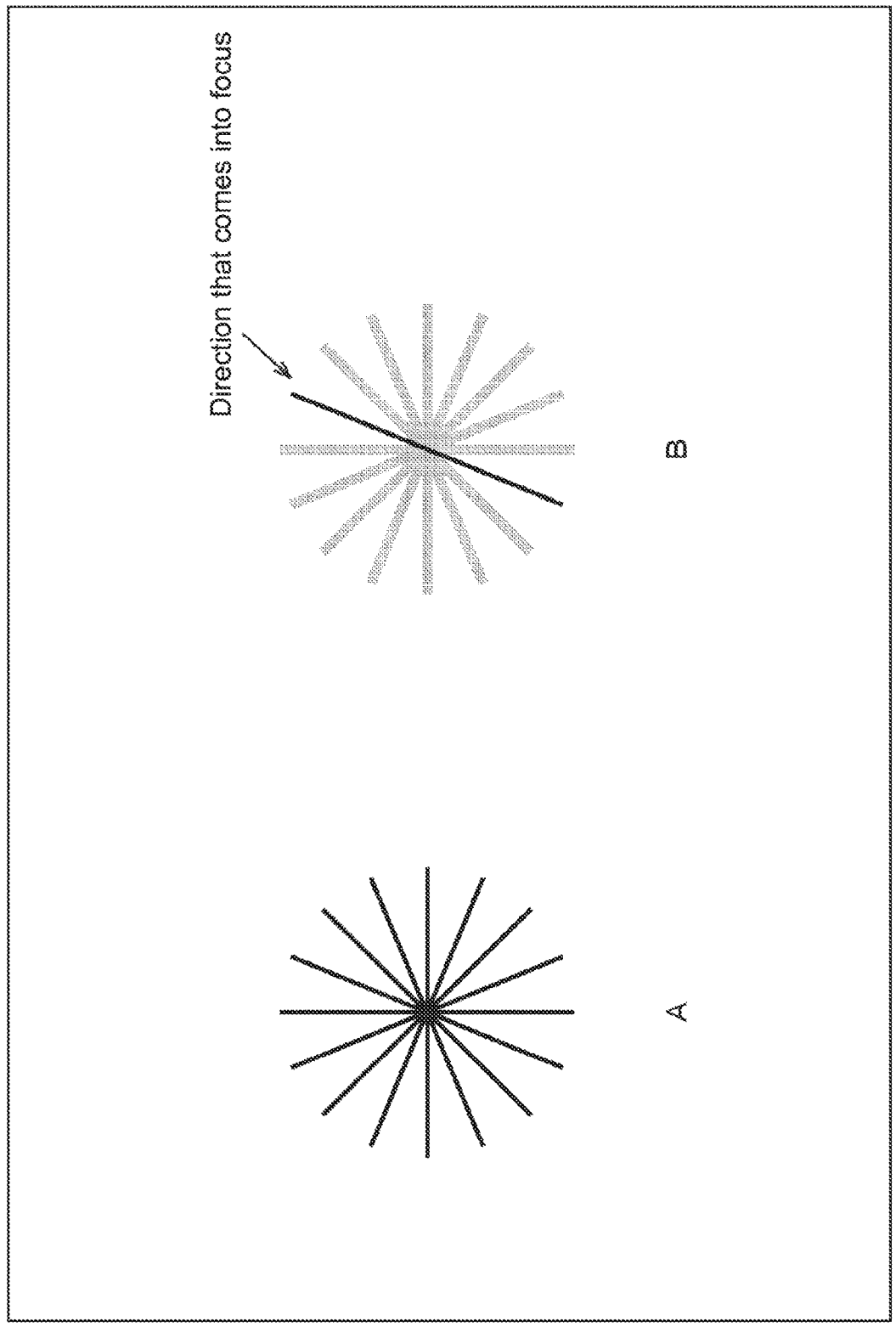
FIG. 7 is a diagram describing an example of a radial pattern.

For example, radial shaped light may be radiated to the object 121 from the optical unit 103 as shown in A of FIG. 7. A method of realizing such a radial light source is arbitrary, but for example, as with FIG. 6, a slit having a radial opening may be provided between the point light source and the astigmatic lens 111.

When the radial light passes through the astigmatic lens 111 and is radiated to the object 121, the spot shape is made so that only a line in the direction of focusing is thin and lines in other directions are thicker than that as an example shown in B of FIG. 7.

Then, the measuring unit 105 may observe the spot shape of the radiation light in the object 121 detected in the detecting unit 104, obtain how close the object 121 is to one of a plurality of focal positions based on a degree of change in its shape, that is, the extent to which each line of the radial spot shape is thick, and obtain the distance (L) to the object 121.

Thus, by forming the radiation shape into the radial shape, a line of direction inclined to the cross-shape is also added to a thickness measurement target. Therefore, for example, even if a direction of aberration is displaced from a linear direction of the radiation light when the astigmatic lens 111 is attached, it is possible to further reduce a generation of false recognition and measure the distance at higher speed and with higher accuracy.

It should be noted that an interval (angle) of each radial line may be uniform or non-uniform. Also in this case, similarly to the case of the slit having the cross-shaped opening, the light emitting unit 102 may have the slit. Moreover, instead of the slit, a light guide plate having a waveguide whose surface shape is formed into a radial shape may be provided. Further, instead of the slit, the diffractive optical element (DOE) may be used to radiate radial light.

Measurement of Amount of Blurring

Plurality of Radiation Light

Figure 8:
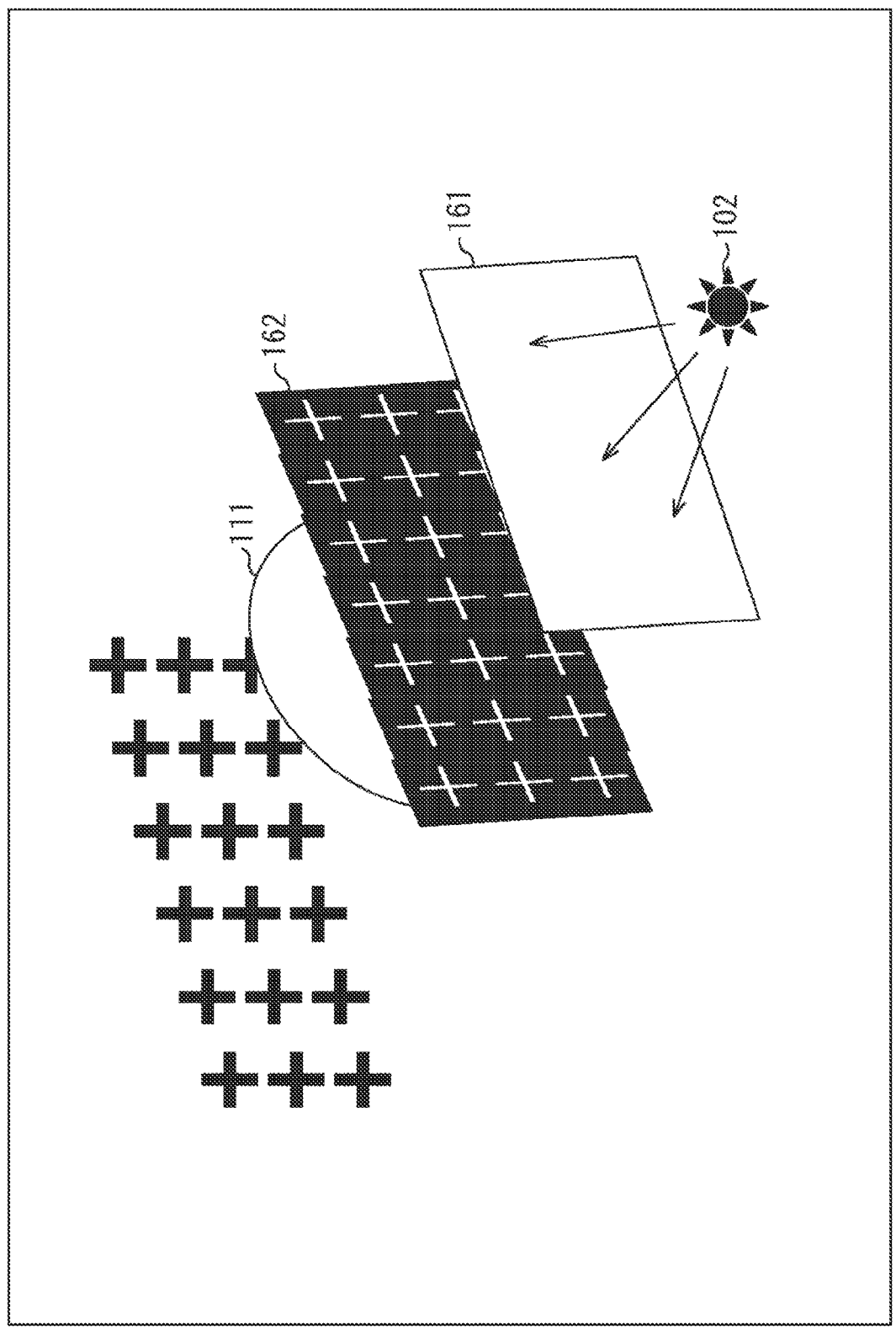
FIG. 8 is a diagram describing an example of a distance measuring method with use of a plurality of cross light sources.

Further, as an example in FIG. 8, a plurality of radiation light may be radiated to the object 121. In the case of the example in FIG. 8, light discharged from a single light source (light emitting unit 102) passes through a light guide plate 161 and a slit 162 having a plurality of openings of a predetermined shape (cross shape in the case of FIG. 8), so that a plurality of radiation light having a predetermined radiation shape is generated. The plurality of radiation light is radiated to the object 121 through the astigmatic lens 111.

This makes it possible to measure a distance for each area of an entire image. It should be noted that in FIG. 8, the plurality of radiation light pass through a single astigmatic lens 111, but the astigmatic lens 111 may be disposed for each radiation light. Moreover, the radiation shape of each radiation light is arbitrary and may be, for example, a radial shape or other shape than the cross shape. Further, as described above, the radiation shapes of the plurality of radiation light and each radiation light may be formed by a waveguide shape and other shapes, instead of the slit 162. For example, the light guide plate which has a plurality of predetermined surface shape waveguides and can provide a plurality of radiation light that forms a predetermined radiation shape can be used instead of the slit 162. Moreover, instead of the slit 162, the diffractive optical element (DOE) may be used to form the radiation shapes of the plurality of radiation light and each radiation light. Moreover, the shape of each radiation light is not necessarily the same. For example, the radiation shape may be different in accordance with the position where the radiation light passes through the astigmatic lens 111.

Measurement of Amount of Blurring

Stripe Shape

Moreover, the radiation shape may be a stripe shape of successive lines as shown in FIG. 9. Namely, for example, the radiation light of a check pattern of A of FIG. 9 and a stripe shape pattern with a plurality of inclined lines of B of FIG. 9 may be radiated to a part or an entire angle of view detected by the detecting unit 104. Thus, by forming the radiation shape into the pattern constituted of a larger number of lines than the radiation shape described above, the measuring unit 105 can determine whether any part of the line in any direction of the pattern comes into focus (becomes thin) or comes out of focus (becomes thick). Namely, the measuring unit 105 can measure the distance in more detail. It is obvious that the pattern of this radiation shape is arbitrary and is not limited to the example of FIG. 9. For example, the pattern may be a pattern including a curve line. Moreover, as the pattern shown in FIG. 9, the pattern is not necessarily an entirely uniform pattern and may be different in accordance with the position.

It should be noted that a method of realizing this pattern is arbitrary. For example, the slit may be used. The pattern may be formed by a waveguide shape and other shapes. The diffractive optical element (DOE) may be used.

Laser Light

Figure 10:
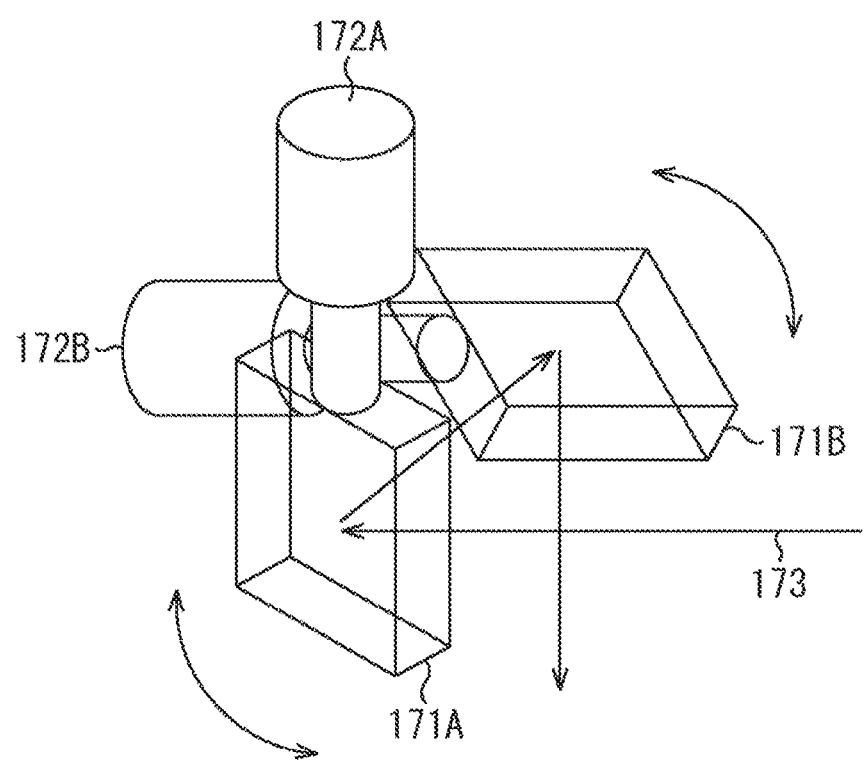
FIG. 10 is a diagram describing an example of a galvanometer mirror.

It should be noted that the light emitting unit 102 may radiate laser light as the radiation light. On this occasion, as shown in FIG. 10, the optical unit 103 includes a biaxial galvanometer mirrors 171A and 171B for reflecting the laser light, and the galvanometer mirrors may scan the laser light from the light emitting unit 102 to radiate the pattern.

The galvanometer mirror 171A can change its direction by driving a motor 172A. The galvanometer mirror 171B can change its direction by driving a motor 172B. Hereinafter, the galvanometer mirror 171A and the galvanometer mirror 171B are simply referred to as the galvanometer mirror 171 if a description is not necessary for distinguishing from each other. Moreover, the motor 172A and the motor 172B are simply referred to as the motor 172 if a description is not necessary for distinguishing from each other. By reflecting laser light 173 by the biaxial galvanometer mirror 171 as shown in FIG. 10, the laser light 173 can be radiated in an arbitrary direction. That is, the control unit 101 drives these motors 172 and controls the direction of the galvanometer mirror 171, which makes it possible to control the radiation direction of the laser light 173. Therefore, for example, as shown in FIG. 9, the laser light can be radiated to the stripe shape pattern. It should be noted that the scan can also be made by the galvanometer mirror by using the lens to form even spontaneous emission light such as LED into collimated beam, instead of the laser light.

Infrared Light

Moreover, the light emitting unit 102 may radiate infrared light as the radiation light. By using the infrared light, a human eye is hard to sense it, so that distance information can be obtained without much concern that the light is radiated. Therefore, for example, this can apply to a signal input by a game and a gesture and like.

Also in the case where the radiation light is the infrared light, a detecting method and a distance measuring method can adopt basically the same method as that for visible light.

Figure 11:
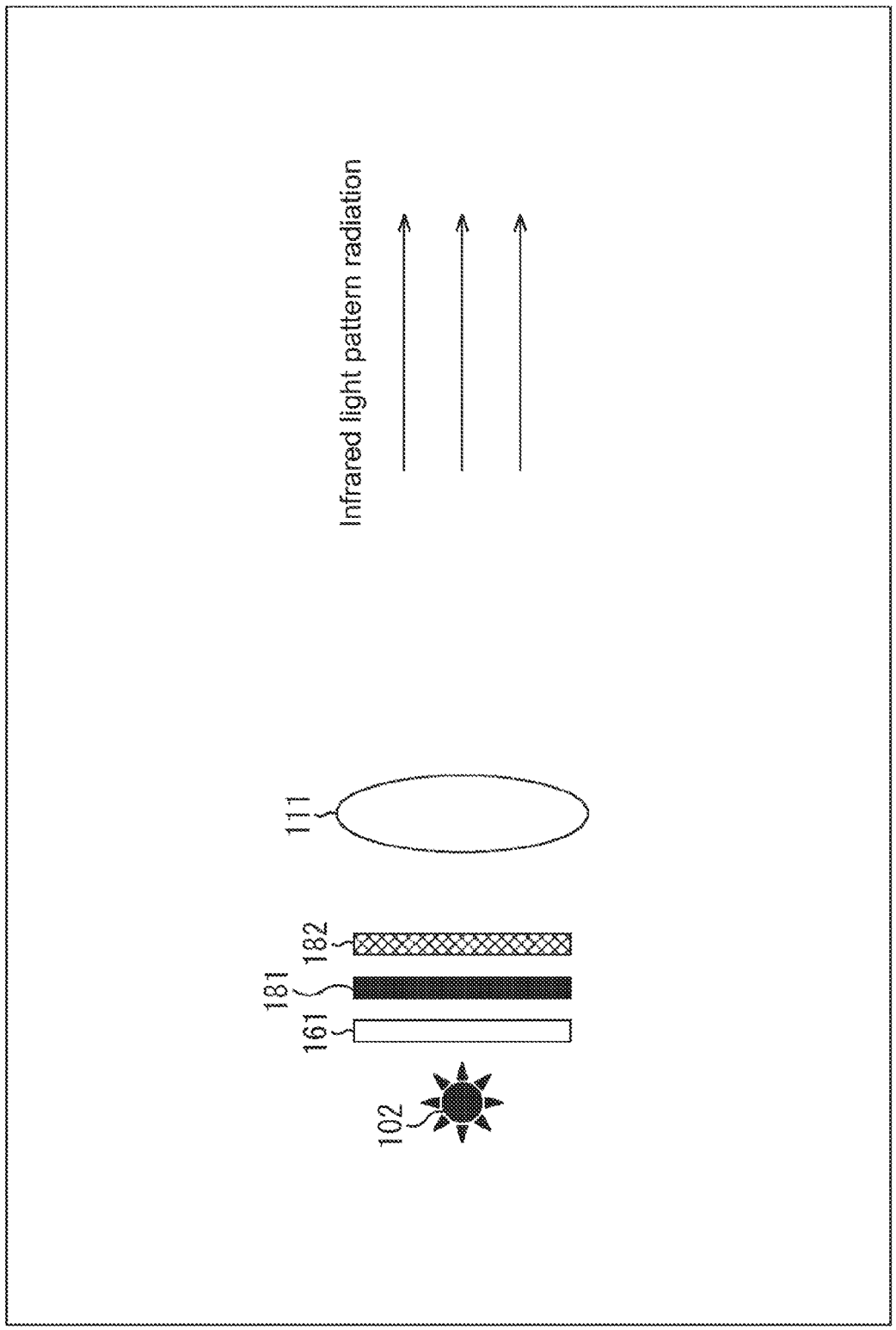
FIG. 11 is a diagram describing an example of a distance measuring method with use of infrared light.

It should be noted that the light source which the light emitting unit 102 has is arbitrary and may be LED, a laser, a lamp and the like, for example. In the case of the lamp, as shown in an example of FIG. 11, an infrared light cut filter 182 that cuts the visible light and allows the infrared light to transmit through may be used in addition to the light guide plate 161 and a slit 181. Herein, the light guide plate 161 is used to be configured to form uniform in-plane light intensity radiation. For example, the opening with an arbitrary pattern having various patterns described above may be provided to the slit 181. Moreover, instead of the slit 181, the light guide plate including the waveguide that forms the surface shape of the arbitrary pattern having the various patterns described above may be provided. As a further alternative method, instead of the slit 181, the diffractive optical element (DOE) may be used to radiate light that forms the arbitrary pattern shape. In the example of FIG. 11, the infrared light cut filter 182 is provided between the slit 181 and the astigmatic lens 111, but this position is arbitrary. Moreover, the lamp may be replaced with the LED and the laser, but in this case, the infrared light cut filter 182 can be omitted.

Figure 12:
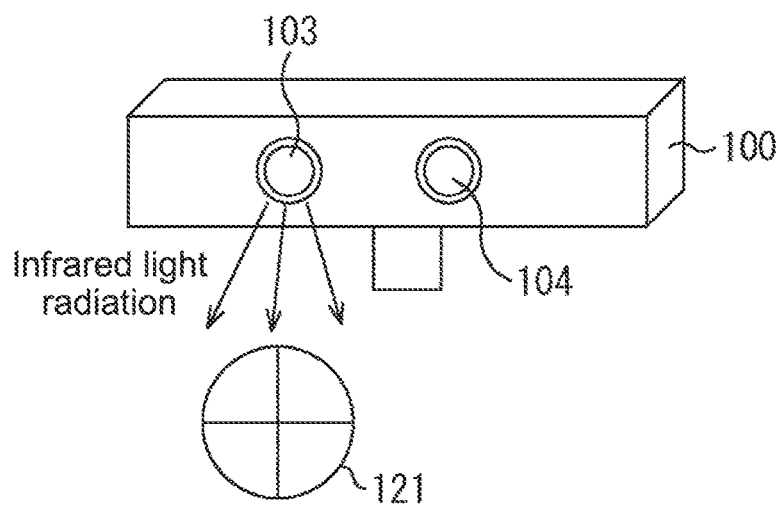
FIG. 12 is a diagram describing an example of an image sensor.

The detecting unit 104 (image sensor side) may be any apparatus as long as infrared light can be detected. However, for example, in the case of an apparatus or a system for obtaining an image of visible light as in a normal imaging, it may be configured such that the detecting unit 104 can detect the infrared light and obtain the image of the visible light as shown in FIG. 12, for example. This eliminates the necessity to provide two types of image sensors for visible light and infrared light and can reduce the cost. Moreover, this matches detection positions of the visible light and the infrared light (no displacement occurs), so that the distance can be measured more precisely.

Figure 13:
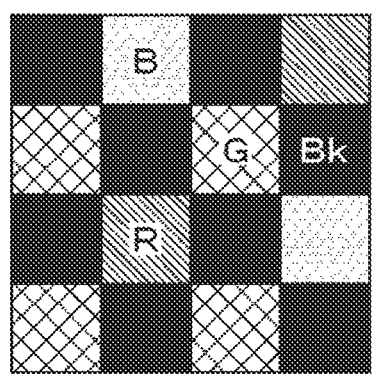
FIG. 13 is a diagram describing an example of a pixel arrangement.

In that case, a pixel arrangement of the image sensor of the detecting unit 104 may be formed as an example of FIG. 13. The image sensor shown in the example of FIG. 13 is constituted of a pixel to which a red filter (R) is allocated (also referred to as R pixel), a pixel to which a green filter (G) is allocated (also referred to as G pixel), a pixel to which a blue filter (B) is allocated (also referred to as B pixel), and a pixel to which a black filter (Bk) is allocated (also referred to as Bk pixel). In the visible light, spectrum of R, G, and B functions to allow light of red, green, and blue regions to transmit through and block light in other regions. However, the infrared light transmits through these filters. In contrast, Bk functions to block the visible light and allows the infrared light to transmit through.

Figure 14:
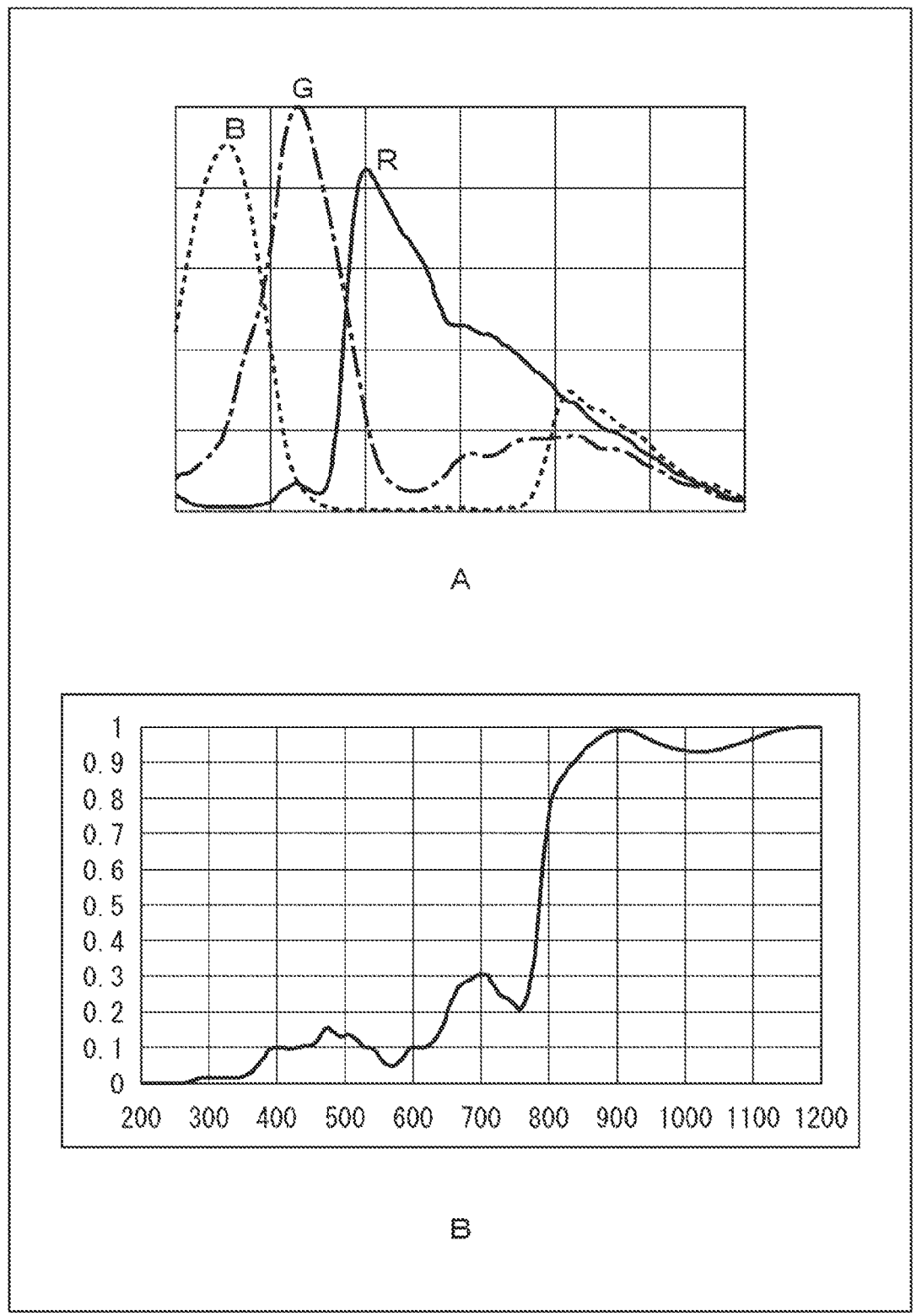
FIG. 14 is a diagram describing an example of a spectral characteristics.

FIG. 14 shows an example of such spectrum. A of FIG. 14 is a graph showing transmission characteristics of each filter of R, G, and B, and B of FIG. 14 is a graph showing transmission characteristics of Bk. It should be noted that A of FIG. 14 shows the spectrum of R, G, and B as a spectral sensitivity curve when the filter is placed on a photodiode of silicon (Si). Moreover, B of FIG. 14 shows the spectrum of Bk as transmittance spectral characteristics of the filter.

From this spectral characteristics, an image of the infrared light is obtained by using Bk pixel. In contrast, the image obtained from R pixel, G pixel, and B pixel turns out to be images of the visible light and the infrared light. Accordingly, the image obtained from R pixel, G pixel, and B pixel has poor performance in color reproducibility and increases color difference. To avoid this problem, a true value of a red component (R*), a true value of a green component (G*), and a true value of a blue component (B*) may be obtained by an arithmetic expression as shown in FIG. 15, and a normal white balance and linear matrix operation may also be performed. This can improve color reproducibility of the image of the visible light obtained from R pixel, G pixel, and B pixel.

Figure 16:
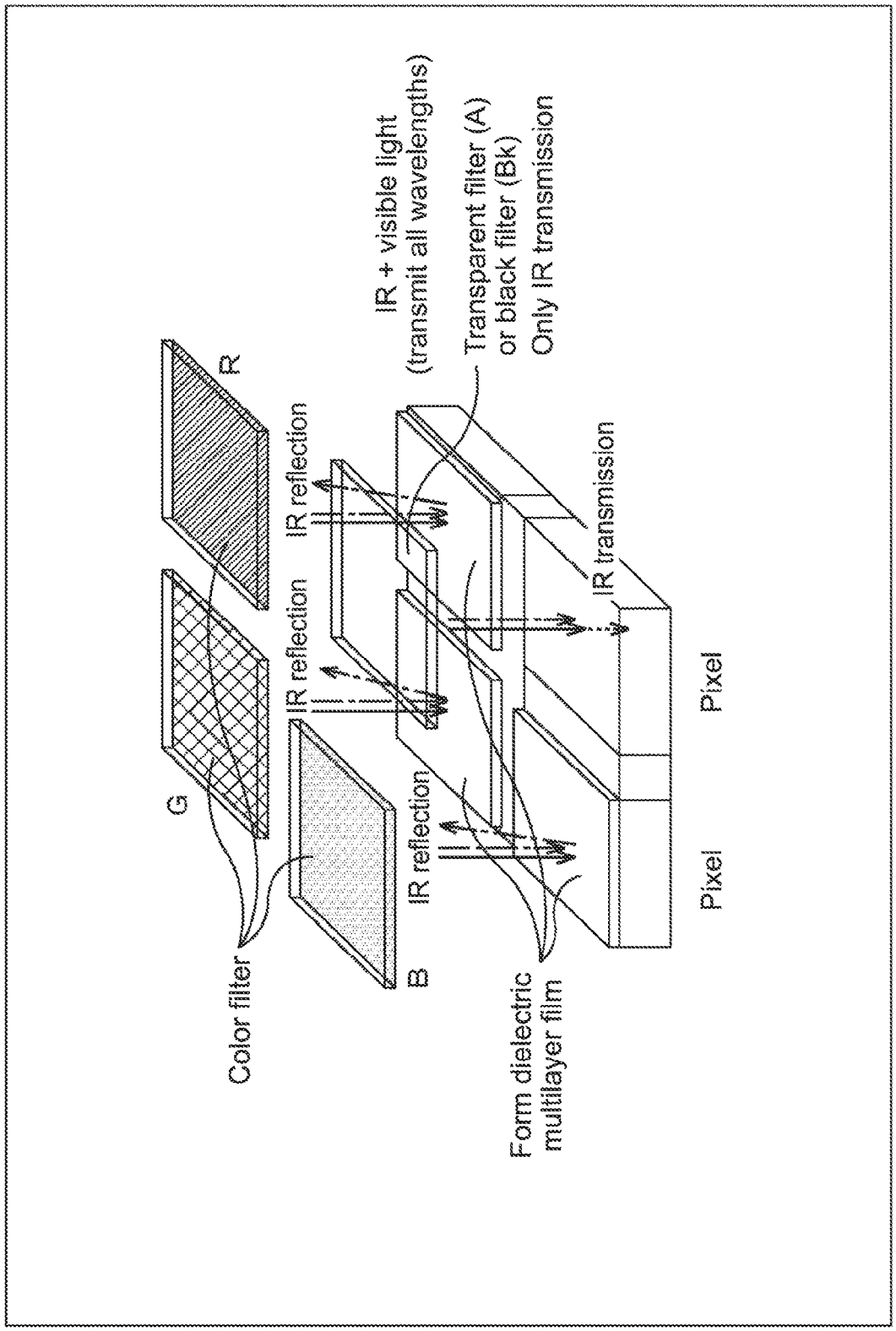
FIG. 16 is a diagram showing an example of a pixel configuration.

FIG. 16 shows an example of a bird's eye view of the image sensor capable of simultaneously obtaining the infrared/visible image described above. In this case, as a pixel for obtaining the image of the infrared light, there is a pixel to which the black filter Bk that allows only infrared light to transmit through or a transparent filter A that allows both of the infrared light and the visible light to transmit through is allocated. The pixel arrangement may be arranged as shown in FIG. 13.

A visible light pixel for obtaining the image of the visible light includes the color filters of RGB at the top thereof and forms a dielectric multilayer film which reflects the infrared light and allows the visible light to transmit through at the bottom thereof. This can reduce an infrared component which enters the underlying photodiode (PD). By configuring the image sensor as described above, it is possible to omit a color correction calculation as described above with respect to FIG. 15 and improve color reproducibility.

Figure 17:
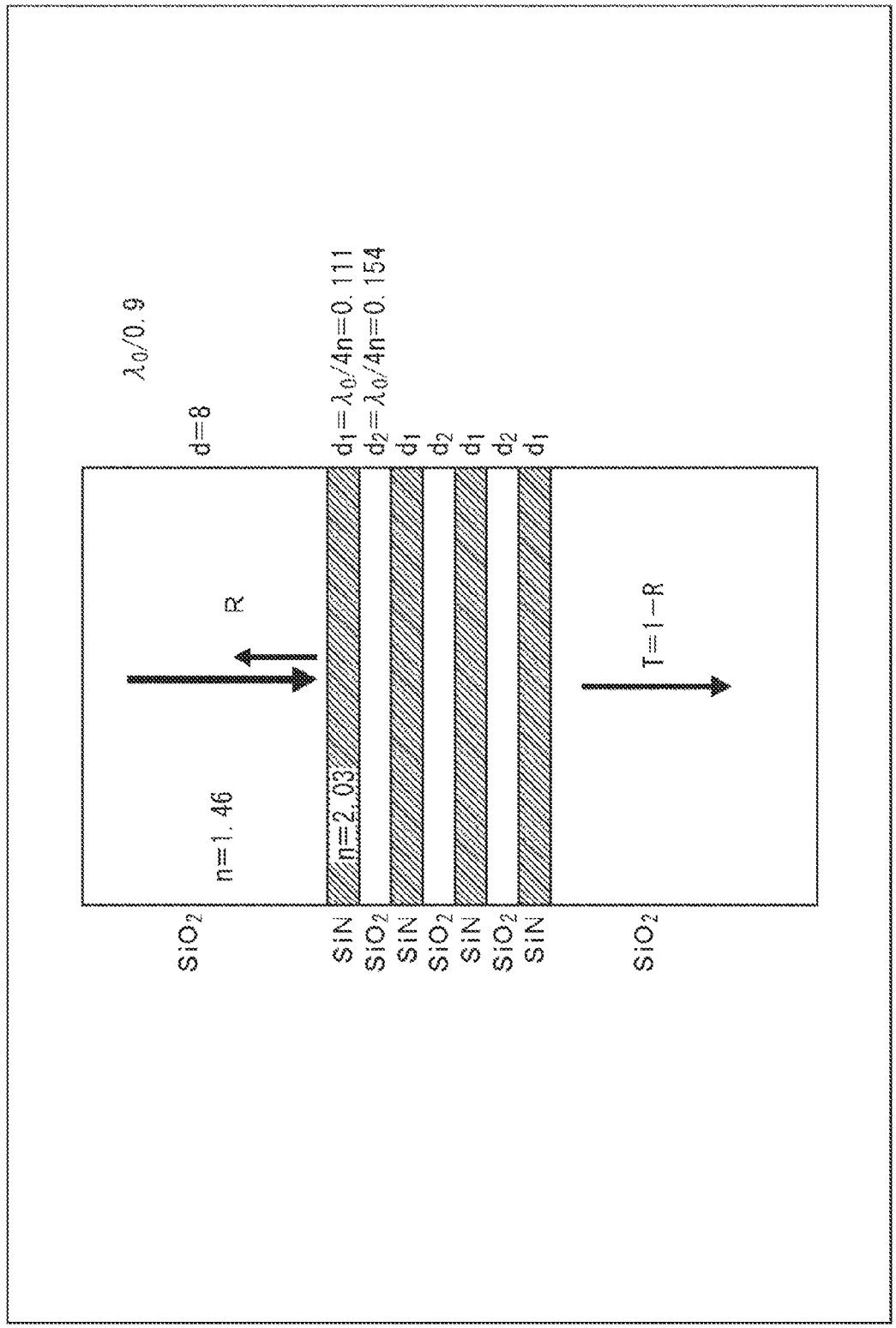
FIG. 17 is a diagram showing a configuration example of a dielectric multilayer film.
Figure 18:
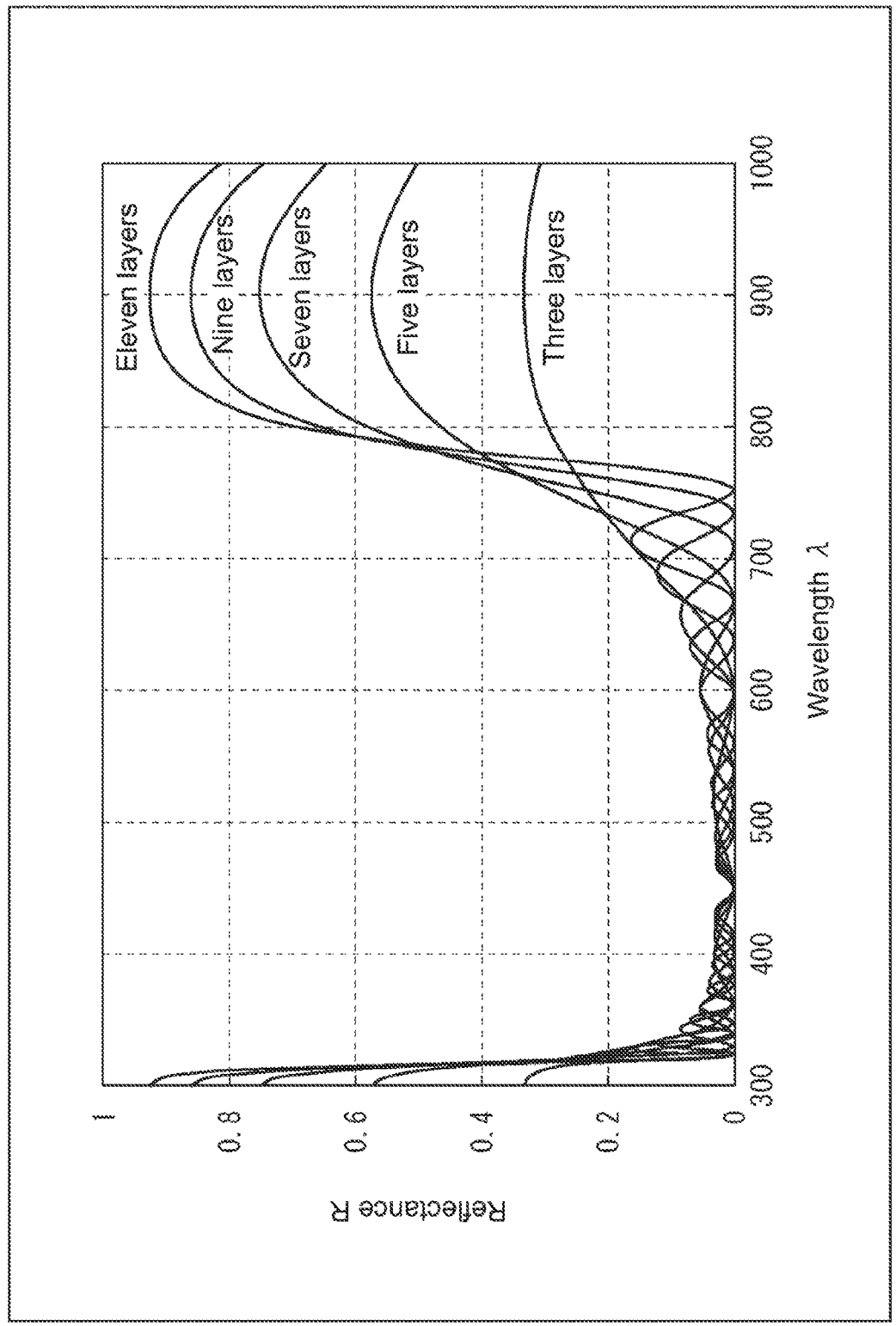
FIG. 18 is a diagram showing an example of a reflection property of the dielectric multilayer film.

Herein, FIG. 17 shows a configuration example of the dielectric multilayer film which reflects the infrared light and allows the visible light to transmit through. In the example shown in FIG. 17, the dielectric multilayer film is formed of a multilayer film of silicon nitride ($Si_3N_4$ (SiN)) and silicon dioxide ($SiO_2$). Moreover, FIG. 18 shows a relationship between the number of the dielectric multilayer film and reflectance. From FIG. 18, it can be seen that the multilayer film having eleven layers reflects 90% or more of the infrared light.

It should be noted that when a filter having an infrared light pixel is transparent, the filter allows both the infrared light and the visible light to transmit through, which is also advantageous in achieving higher sensitivity and simultaneously enables the distance measurement.

By arranging as described above, the distance measuring apparatus 100 can perform the distance measurement with higher performance.

Astigmatic Lens Shape

Next, the astigmatic lens 111 will be described. Astigmatism is generated by a thin portion and a thick portion (non-uniformity in thickness) surrounding the lens in a concentric direction. The shape of the astigmatic lens 111 may be any shape as long as the shape generates the astigmatism, that is, the shape has non-uniformity in thickness surrounding the lens in the concentric direction. For example, the astigmatic lens 111 may have a shape configured such that the focal lengths do not change in a radial direction (sagittal) from a central side of the astigmatic lens 111 toward a peripheral side and the focal lengths continuously change in a concentric direction (meridional) centered at one of the center of the astigmatic lens 111 and a vicinity of the center.

Figure 19:
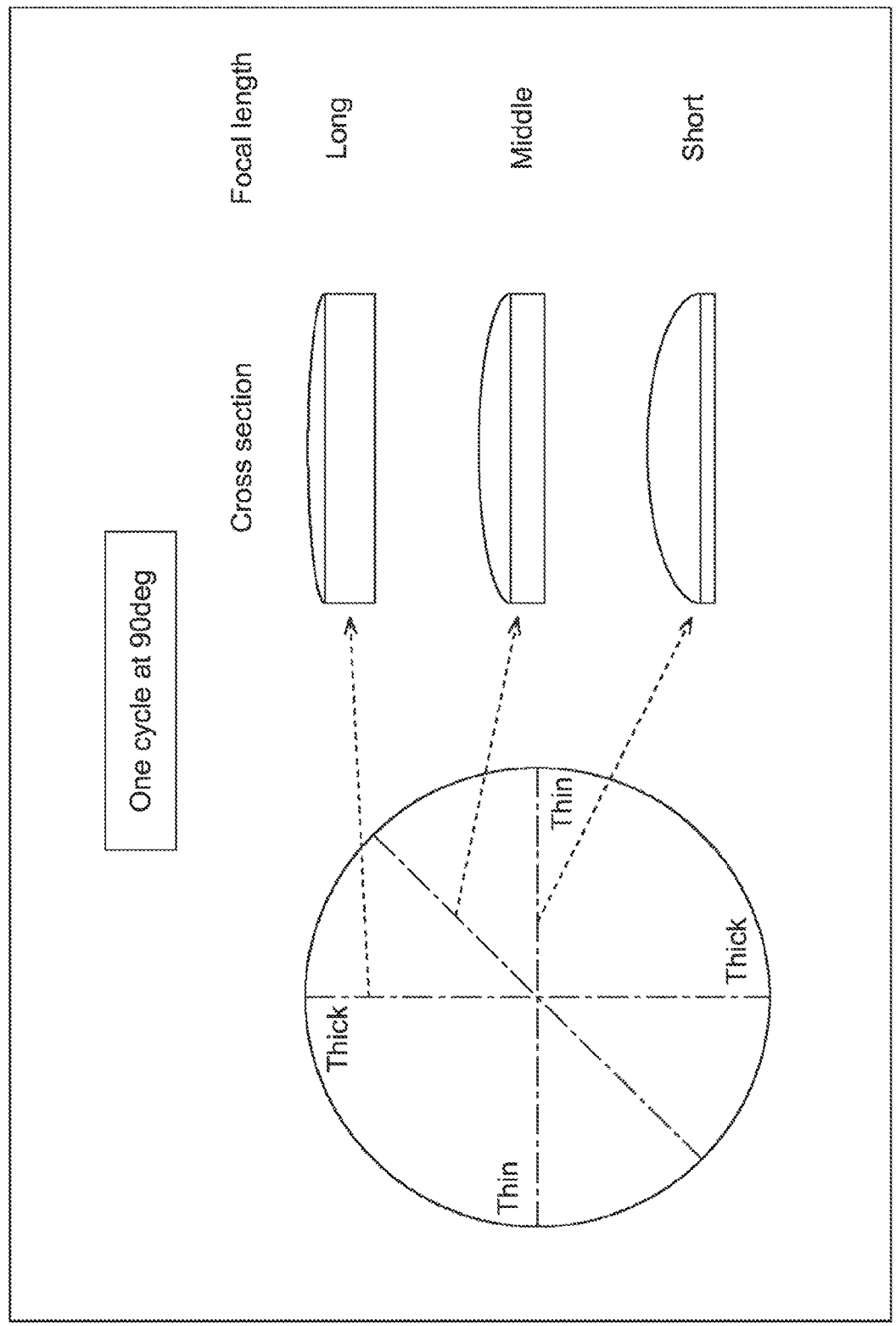
FIG. 19 is a diagram showing an example of a shape of the astigmatic lens.
Figure 20:
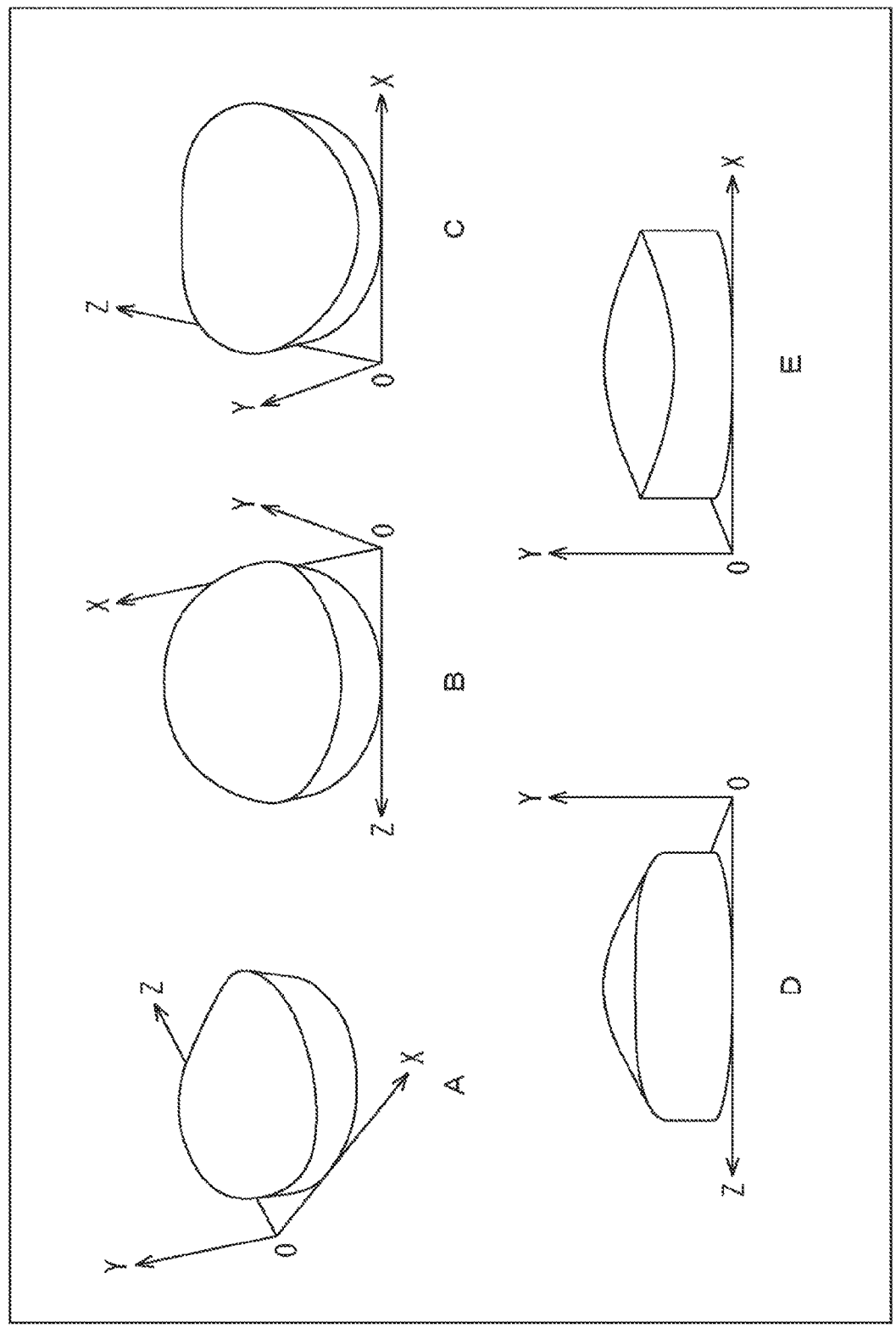
FIG. 20 is a diagram showing an example of the shape of the astigmatic lens.

For example, as shown in FIG. 19, a circumference of the lens may be shaped in a manner of thin→thick at a rotation of 90 degrees (90deg) in the concentric direction. A to E of FIG. 20 show bird's eye views of the shape. A to E of FIG. 20 are diagrams showing a state where the astigmatic lens 111 disposed in a space represented by three axes XYZ is seen from respective viewpoints. At the thick portion of the circumference of the lens, the focal length increases as a radius of curvature of a cross-sectional shape of the lens increases. In contrast, at the thin portion of the circumference of the lens, the focal length decreases as the radius of curvature of the cross-sectional shape of the lens decreases. When this thickness is placed in the middle, an intermediate focal length is obtained. In the case of an example in FIG. 19, at the rotation of 90 degrees (90deg), the thickness is changed in a manner of thin→thick, so that even a slight displacement may increase an amount of change of the focal length.

Figure 21:
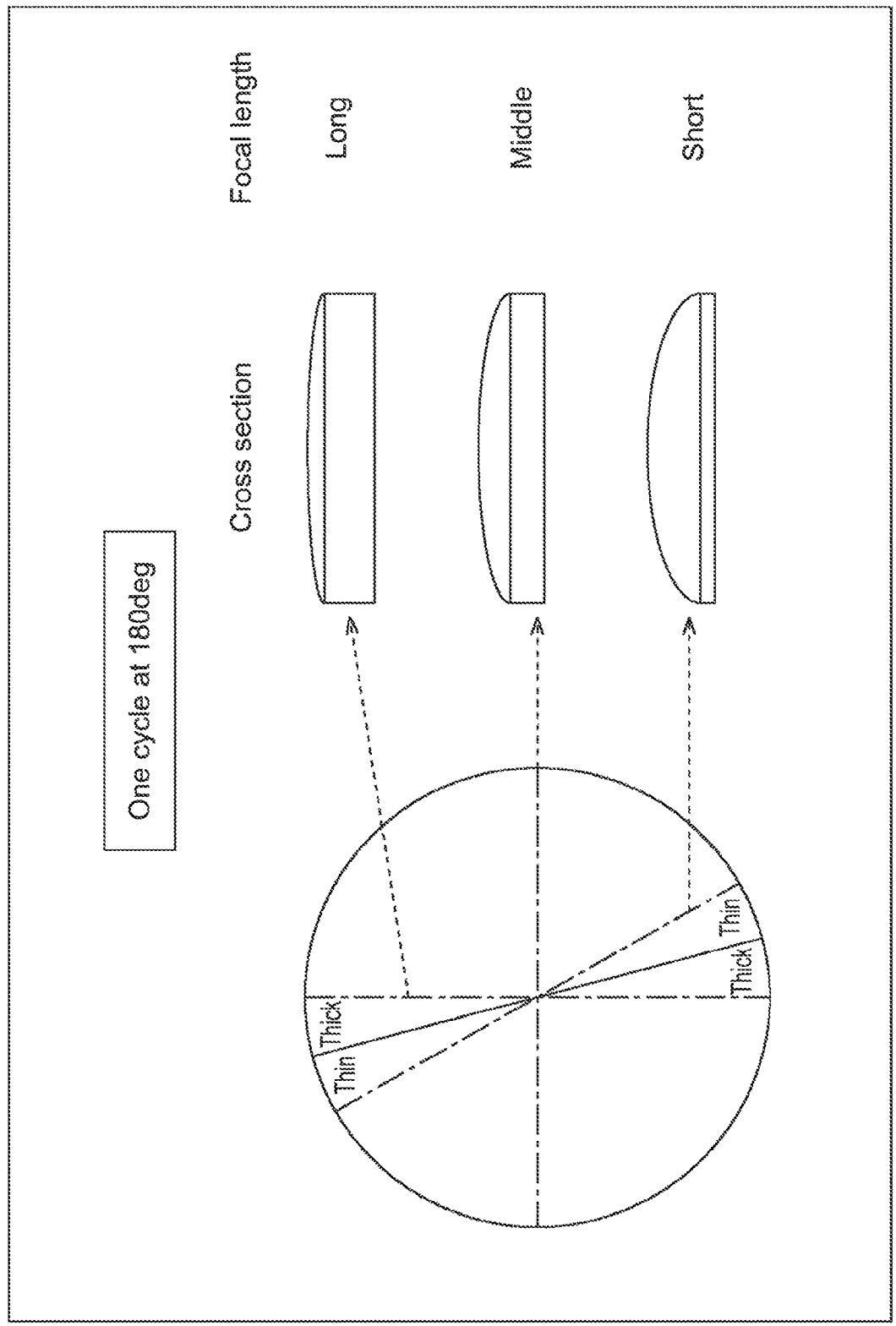
FIG. 21 is a diagram showing an example of the shape of the astigmatic lens.
Figure 22:
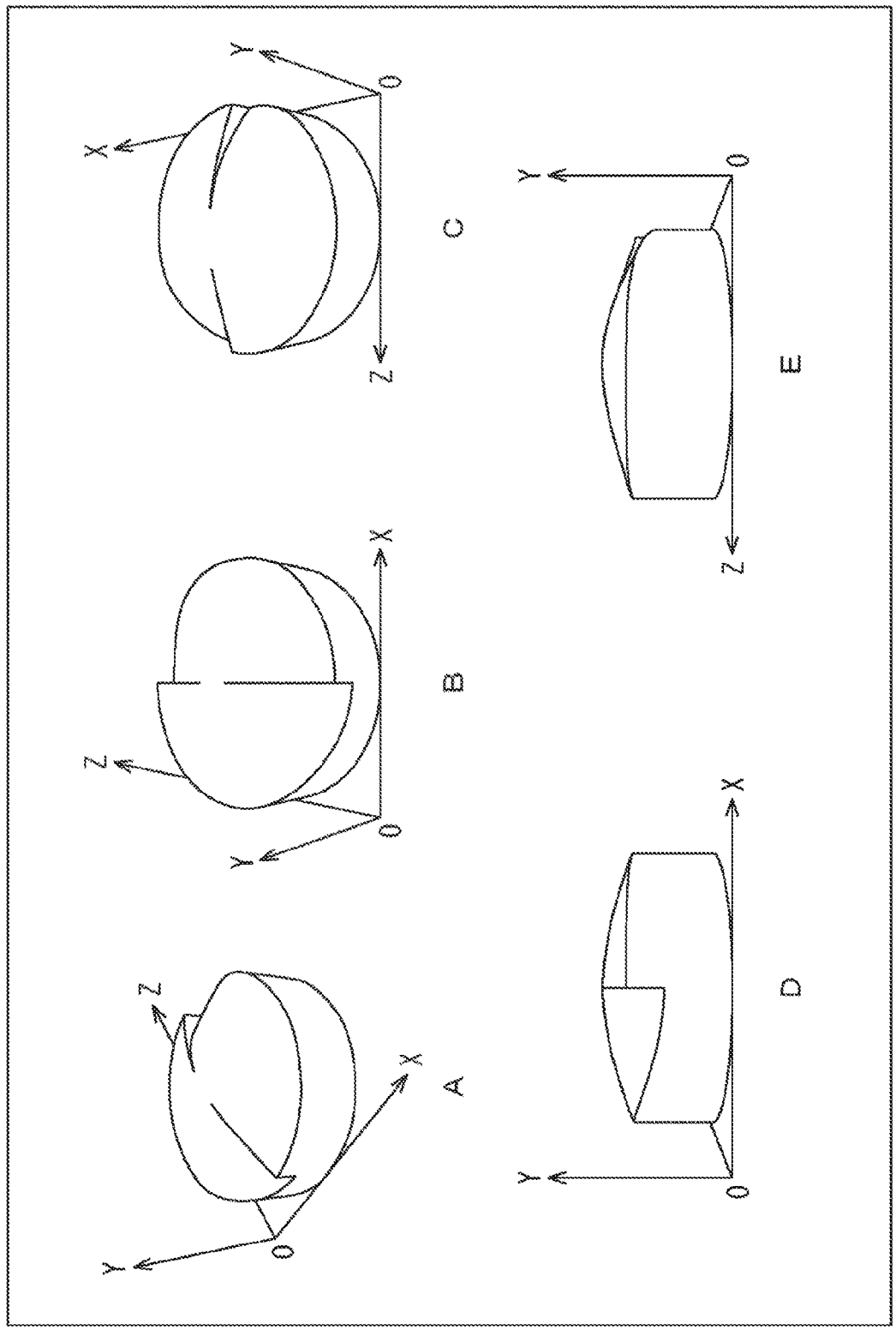
FIG. 22 is a diagram showing an example of the shape of the astigmatic lens.

Then, as shown in FIG. 21, the circumference of the lens may be shaped in a manner of thin→thick at the rotation of 180 degrees (180deg). A to E of FIG. 22 show bird's eye views of the shape. A to E of FIG. 22 are diagrams showing a state where the astigmatic lens 111 disposed in a space represented by three axes XYZ is seen from respective viewpoints. In this case, in comparison with the example of FIG. 19, the thickness gradually changes in the concentric direction and the focal length also changes moderately, so that the accuracy can be improved. In particular, the radiation shape is formed into the radial shape as shown in the example of FIG. 7, which makes it possible to improve the accuracy. The radial light as shown in the example of FIG. 7 and the astigmatic lens of FIG. 21 are combined, and the measuring unit 105 checks which direction of the line has the best focus, that is, whether the line is thinned, so that the distance measurement accuracy can be improved remarkably.

Convertible Lens

It should be noted that the astigmatic lens 111 may be constituted of a plurality of lenses. Moreover, the astigmatic lens 111 may be a convertible lens having the focal length variable.

Figure 23:
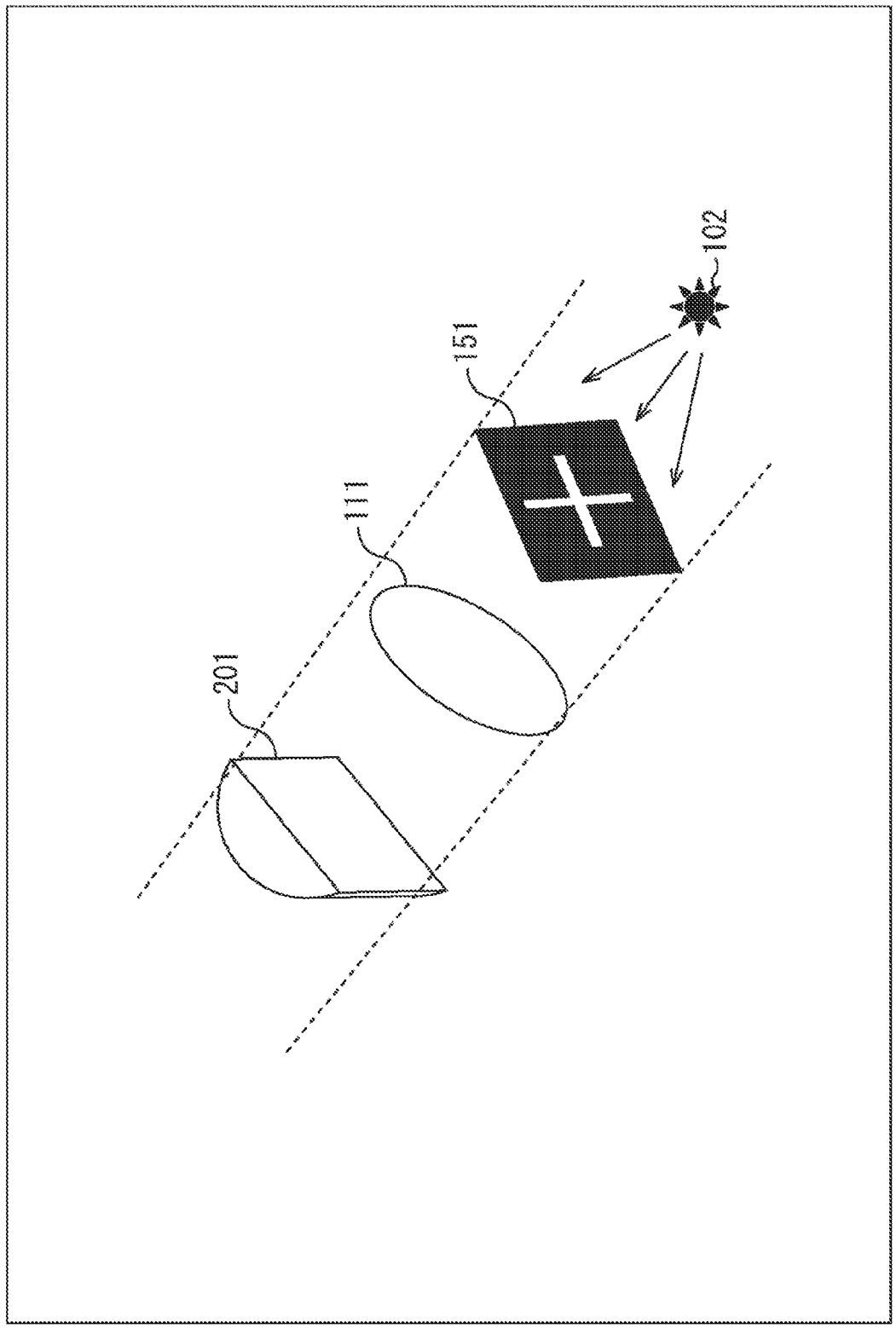
FIG. 23 is a diagram showing an example with use of a lenticular lens.

For example, as shown in an example of FIG. 23, it may be configured such that a semicylindrical (lenticular) liquid lens 201 is combined with the astigmatic lens 111 having a fixed focal point and the focal length of a crisscross vertical line can be changed. Such a configuration can expand the range in which the distance can be measured.

It should be noted that the radial shape is arbitrary and may be other shape than the cross shape. For example, the radial shape as shown in the example of FIG. 7 may be applied, or the stripe shape as shown in the example of FIG. 9 may be applied. Moreover, a plurality of radiation light may be applied.

Figure 24:
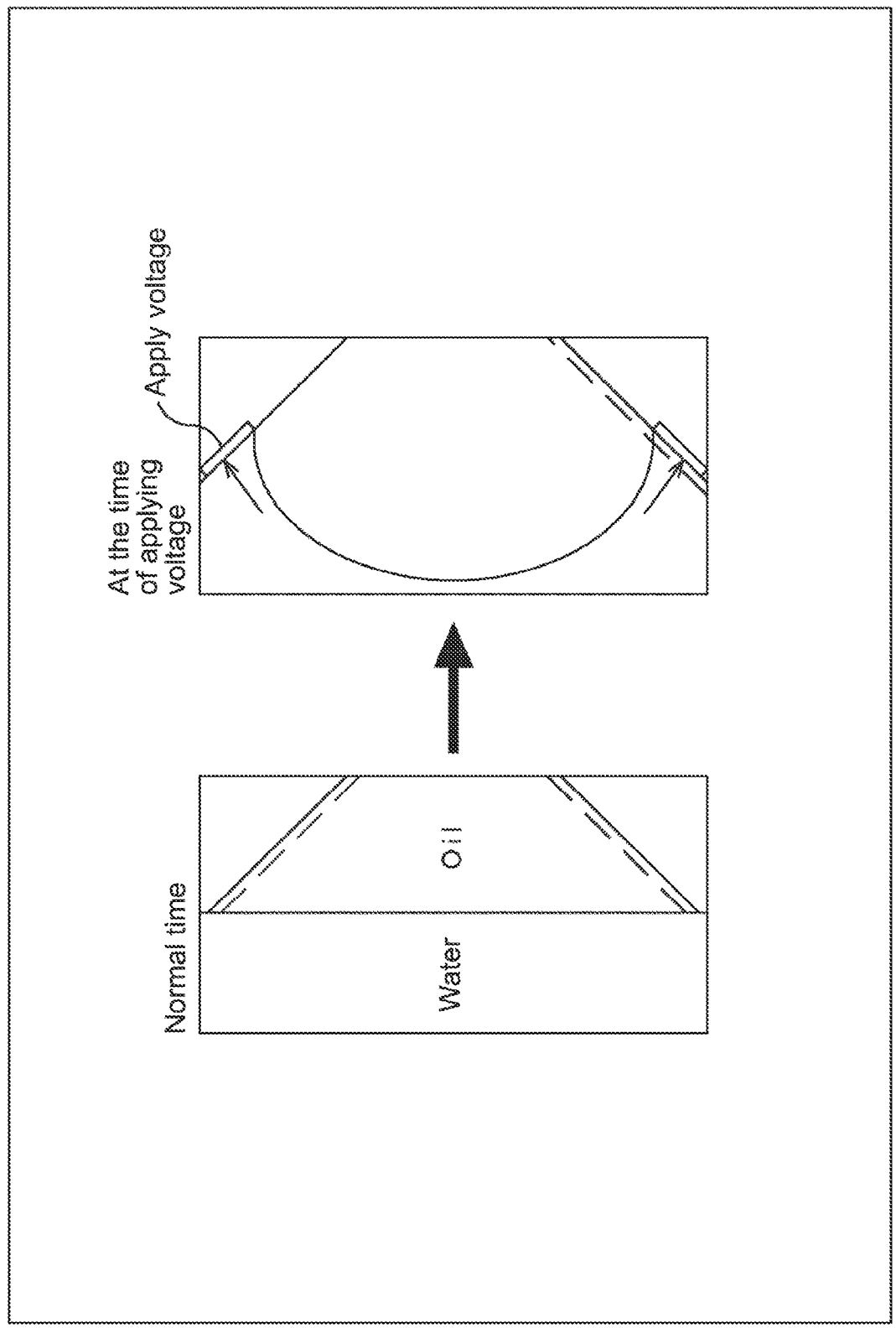
FIG. 24 is a diagram showing an example of a liquid lens.

Meanwhile, as shown in FIG. 24, the liquid lens 201 can change the focal length by changing the shape of the interface between water and oil according to voltage control. In the example of FIG. 23, a lenticular lens is configured such that the focal length can be changed in a predetermined direction. In the case of the example in FIG. 23, the focal length of the light entered from the horizontal direction of the lens is changed, resulting in changing the focal length of the line in the vertical direction of the radiation light.

Figure 25:
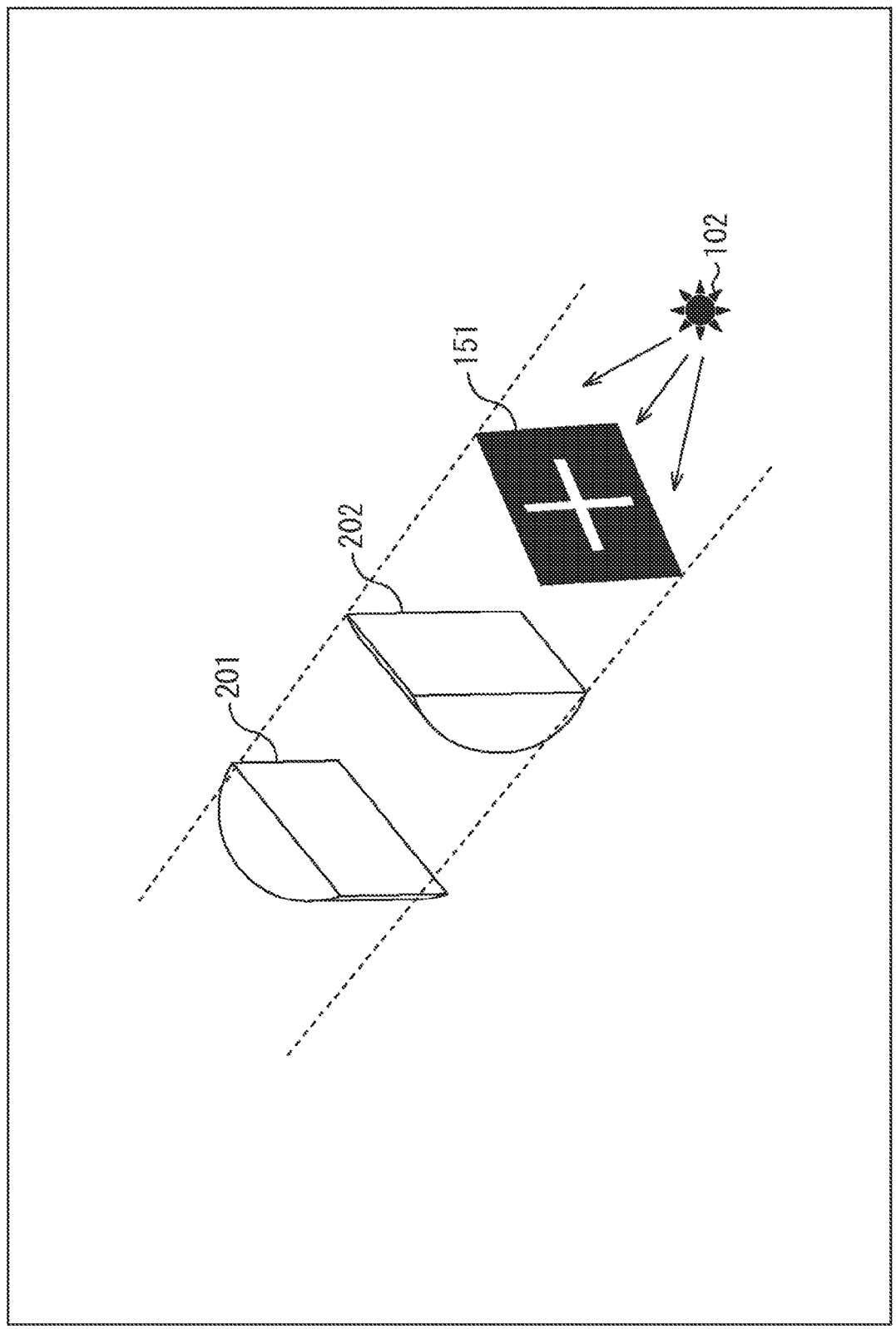
FIG. 25 is a diagram showing an example with use of the lenticular lens.

For example, when the distance measurement is performed at a closer range, a radius of curvature r of the lenticular lens is decreased, thereby decreasing the focal length. On the contrary, when the distance measurement is performed at a longer range, the radius of curvature r of the lenticular lens is increased, thereby increasing the focal length. It should be noted that in the case of the example in FIG. 23, the focal length of the line in the horizontal direction of the radiation light is fixed. It should be noted that instead of the astigmatic lens 111 having a fixed focal length, as shown in FIG. 25, a lenticular lens 202 in the direction rotated by around 90 degrees with respect to the lenticular lens 201 having a variable focal point may be used.

It should be noted that the lenticular lens 202 may be a convertible lens. Moreover, both of the lenticular lenses 201 and 202 may be a convertible lens.

Moreover, three or more lenses may be combined. For example, it may be configured such that three or more convertible lenticular lenses are combined and the focal lengths of the lines in three or more directions can be changed.

Combination of Distance Measuring Method

It should be noted that the distance measuring method with use of the astigmatism described above may be combined with other distance measuring methods. For example, the light cut-off method described in Japanese Patent Application Laid-open No. S62-291509 may be used together. That is, as described above, the distance measuring apparatus 100 shown in FIG. 1 radiate the light to the object 121 serving as the distance measuring target, detects the reflection light reflected by the object 121, and measures the distance to the object 121 based on the change in the spot shape. Further, the distance measuring apparatus 100 may measure a distance based on displacement amount at the position where the object 121 receives the radiation light. Thus, by measuring the distance with use of the plurality of methods, the accuracy can be improved.

It should be noted that as described above, the distance measuring method and the light cut-off method to which the present technology is applied are performed with use of a basically similar system, excluding the distance measuring method, thereby eliminating the necessity to add a new configuration to use both of the methods together. Therefore, both the methods can be easily used together at a low cost. Moreover, even when both the methods are used together, the detection result of the reflection light by the detecting unit 104 can be shared, so that the distance can be measured at higher speed. That is, the accuracy of the distance measurement can be easily improved at higher speed while minimizing a cost increase.

Flow of Distance Measuring Processing

Next, referring to a flowchart in FIG. 26, an example of a flow of distance measuring processing executed by the distance measuring apparatus 100 in FIG. 1 will be described.

When the distance measuring processing is started, the light emitting unit 102 of the distance measuring apparatus 100 emits light to the object 121 serving as the distance measuring target in step S101. The light discharged from the light emitting unit 102 is radiated to the object 121 through the optical unit 103 (astigmatic lens 111). The radiation light reflects by the object 121.

In step S102, the detecting unit 104 detects the reflection light.

In step S103, the measuring unit 105 measures the distance to the object 121 from the detection result of the reflection light detected in step S102 based on the astigmatism generated for the reflection light.

When the distance is measured, the distance measuring processing is completed.

By executing respective processing as described above, the distance measuring apparatus 100 can easily measure the distance with higher accuracy.

Second Embodiment

Authentication Apparatus

The distance measuring method described in the first embodiment can be applied to any apparatus. For example, the distance measuring method can be used to personal authentication.

Figure 27:
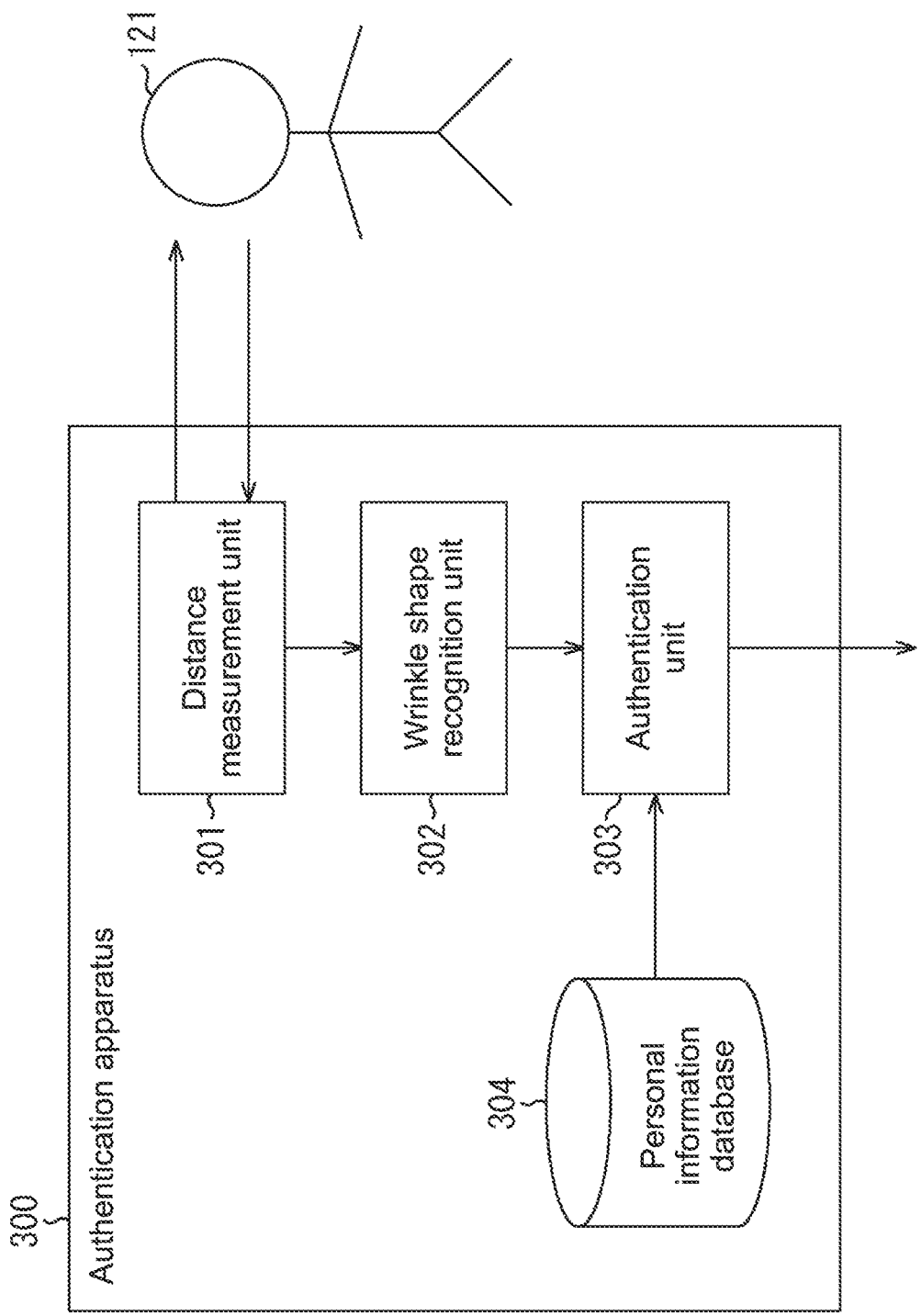
FIG. 27 is a block diagram showing a configuration example of an authentication apparatus.

FIG. 27 is a black diagram is a block diagram showing a main configuration example of an authentication apparatus according to an embodiment of the information processing apparatus to which the present technology is applied.

An authentication apparatus 300 shown in FIG. 27 is an apparatus for performing personal authentication with use of a three-dimensional shape of iris wrinkles of human eyes.

Iris patterns of the human eyes are unique in each individual, unchangeable during the whole life, and different even in identical twins. Moreover, the iris patterns suffer less damage, thereby providing a superior method in identifying individuals. Further, the iris patterns allow non-contact authentication and exhibit a lower feeling of resistance, so that they are widely used now. The personal authentication of the related art simply obtains and compare iris patterns. Since clear iris patterns can be captured, near-infrared light is radiated in many cases. However, this method uses the iris patterns reproduced by printing and the like, so that it is likely to allow unauthorized authentication.

Figure 29:
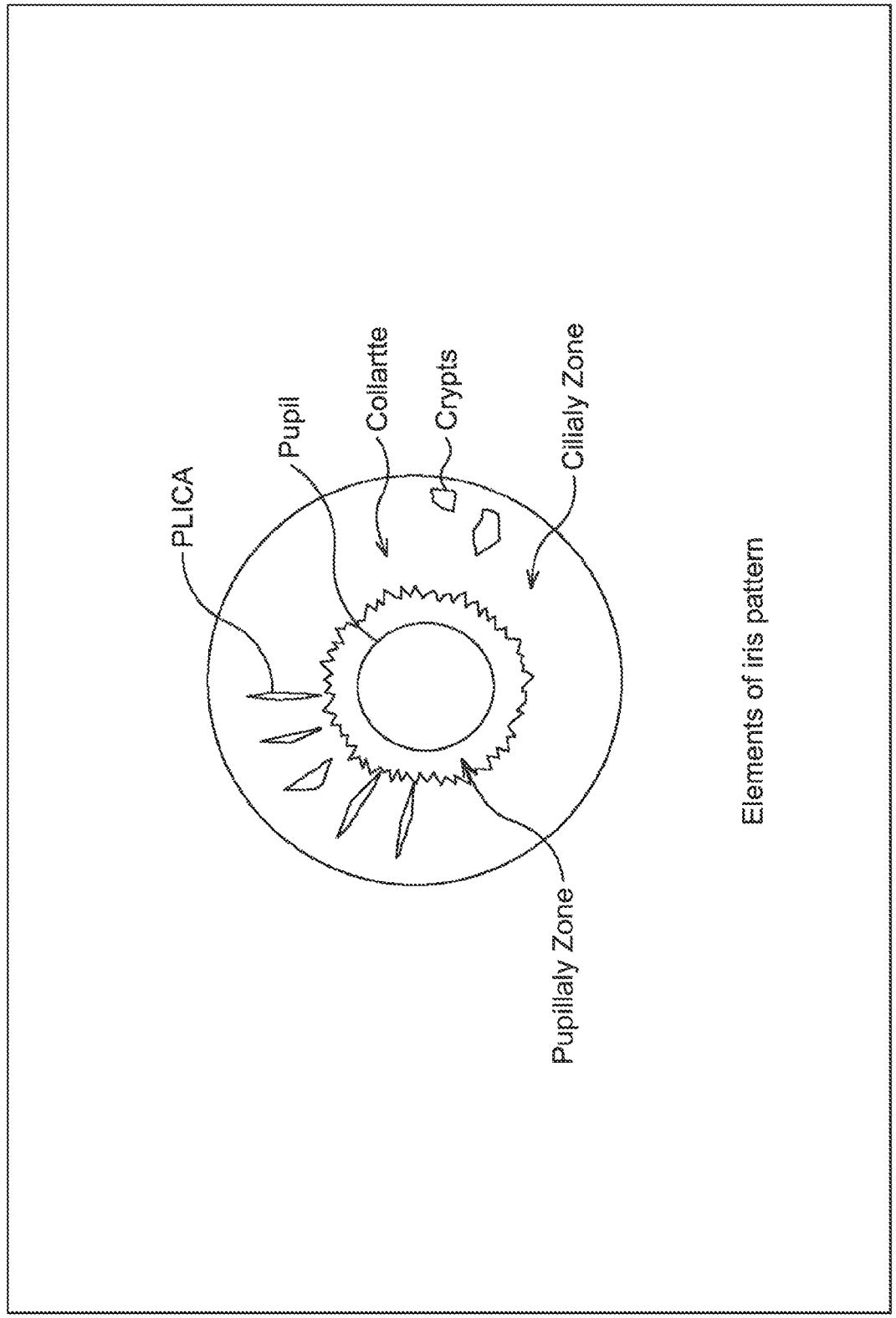
FIG. 29 is a block diagram showing an example of measuring a shape of iris wrinkles.

Meanwhile, as shown in FIG. 29, the iris has various wrinkles. The three-dimensional shape of the wrinkles is unique in each individual, unchangeable during the whole life, and different even in identical twins as with the iris patterns. Moreover, it suffers less damage. Then, the authentication apparatus 300 uses the distance measuring method described in the first embodiment to measure unevenness of the wrinkles, recognize (observe) the shape, and use the shape to perform personal authentication. This can avoid false recognition of a two-dimensional printed counterfeit.

As shown in FIG. 27, the authentication apparatus 300 includes a distance measurement unit 301, a wrinkle shape recognition unit 302, an authentication unit 303, and a personal information database 304.

The distance measurement unit 301 has the same configuration as that of the distance measuring apparatus 100 in FIG. 1 and measures the distance with use of the astigmatism as described in the first embodiment. The distance measurement unit 301 supplies the measurement result (that is, distance information) to the wrinkle shape recognition unit 302.

The wrinkle shape recognition unit 302 is constituted of, for example, a central processing unit (CPU), a random access memory (RAM), a read only memory (ROM) and the like and executes processing regarding the wrinkle shape recognition. Moreover, the authentication unit 303 is constituted of the CPU, the ROM, the RAM and the like and executes processing regarding the personal authentication. The personal information database 304 is constituted of a recording medium such as a flash memory and a hard disk, and performs processing regarding provision of a user's personal information registered in advance. For example, information regarding the three-dimensional shape of the iris wrinkles of the user is registered in the personal information database 304 as information for authentication.

Figure 28:
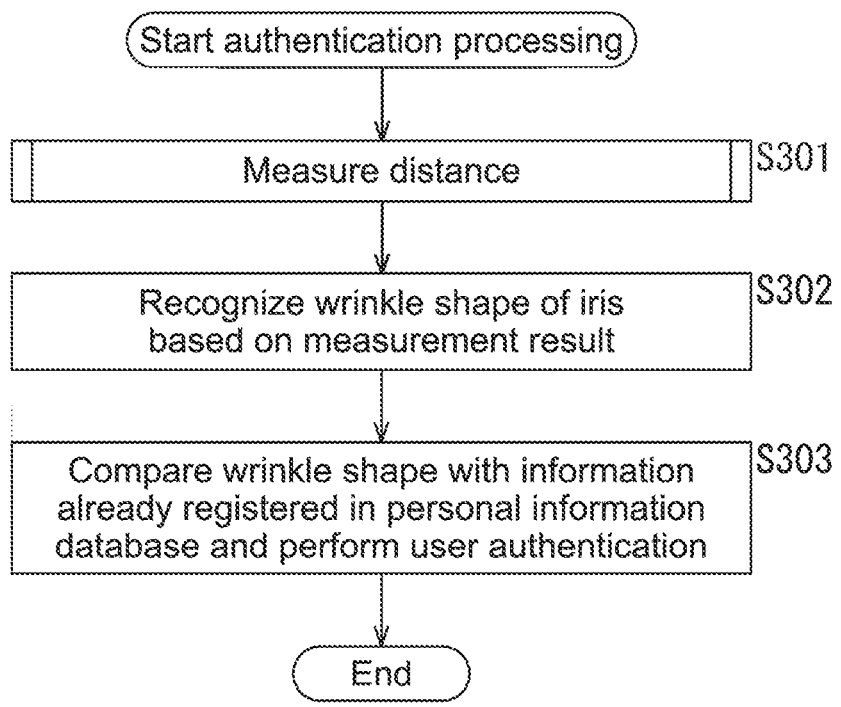
FIG. 28 is a flowchart describing an example of a flow of authentication processing.

When performing the personal authentication of the user (object 121) desiring authentication, the authentication apparatus 300 executes authentication processing. Referring to a flowchart in FIG. 28, an example of a flow of this authentication processing will be described.

Figure 26:
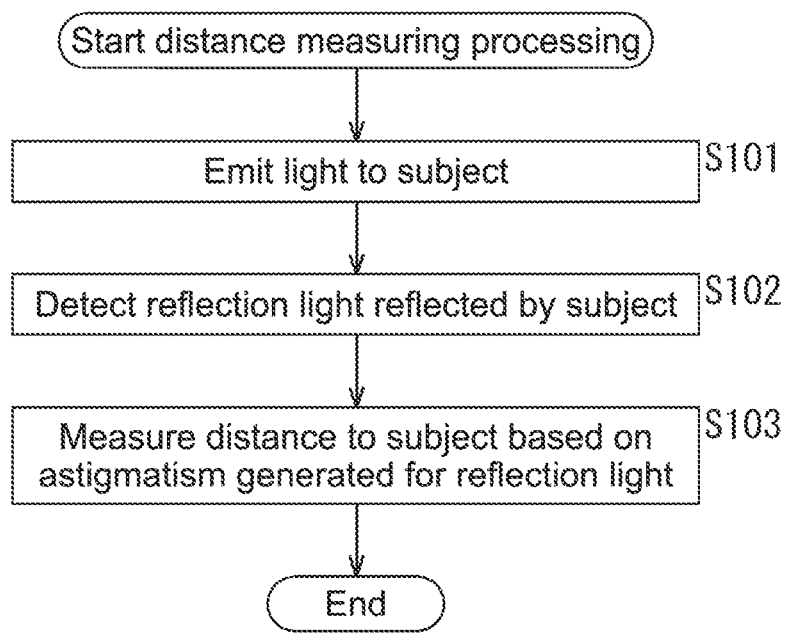
FIG. 26 is a flowchart describing an example of a flow of distance measuring processing.

When the authentication processing is started, in step S301, as described by referring to the flowchart in FIG. 26, the distance measurement unit 301 of the authentication apparatus 300 executes the distance measuring processing and measures, in detail, a distance to the iris of the user (object 121) desiring the authentication. The distance measurement unit 301 supplies the measurement result to the wrinkle shape recognition unit 302.

In step S302, the wrinkle shape recognition unit 302 uses the measurement result obtained by the processing in step S301 to recognize a wrinkle shape of the iris (three-dimensional shape) of the user (object 121). The wrinkle shape recognition unit 302 supplies the recognition result (observed wrinkle shape) to the authentication unit 303.

In step S303, the authentication unit 303 obtains the personal information of the user (object 121) from the personal information database 304, compares the wrinkle shape (observed wrinkle shape) recognized by the processing in step S302 with the information already registered in the personal information database 304, and performs the personal authentication. When the wrinkle shapes of both information are matched, the user (object 121) serving as the authentication processing target is authenticated as an already registered authorized user. Moreover, when the wrinkle shapes are not matched, the user (object 121) serving as the authentication processing target is determined and rejected as an unauthorized user. The authentication unit 303 outputs the authentication result outside the authentication apparatus 300.

When the authentication processing is completed in step S303, the authentication processing is completed.

As described above, by using the present technology (the distance measuring method described in the first embodiment) to perform the personal authentication, the authentication apparatus 300 can deter unauthorized authentication such as impersonation and perform a more precise and safe authentication. It should be noted that the distance measurement unit 301 radiates light toward eyes of the user (object 121), so that it is desirable that light such as infrared light with less influence on the human body be used as the radiation light. Moreover, when visible light is radiated, it is desirable to use light intensity with less influence on the human body.

3. Third Embodiment

Eye Tracking Processing

The distance measuring method described in the first embodiment can be used for eye tracking processing.

Figure 30:
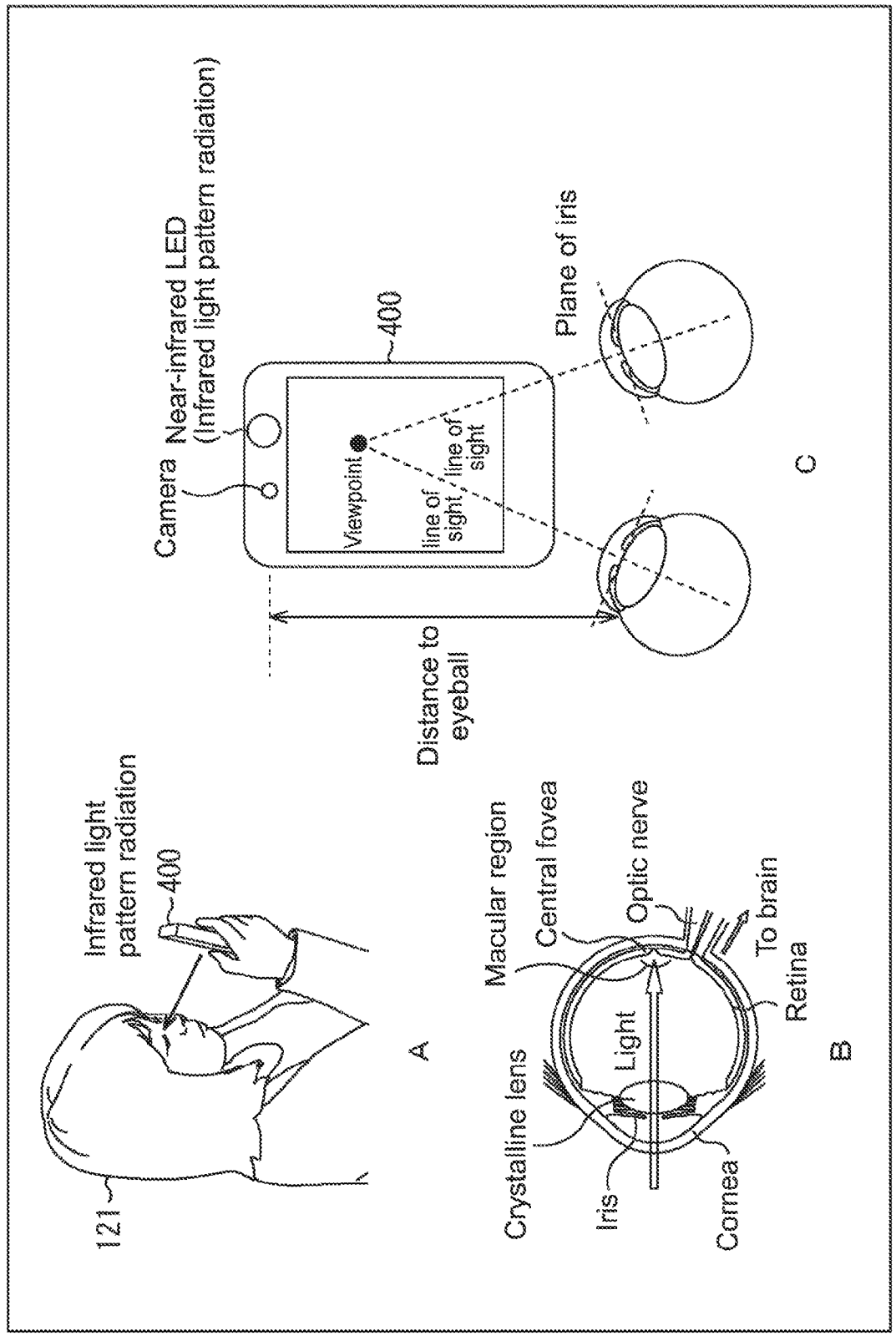
FIG. 30 is a diagram showing an example of a state of an eye tracking.

The eye tracking processing is control processing that an information processing apparatus 400 such as a smartphone and a personal computer detects a movement of eyes of the user (object 121) by a camera and the like and performs processing in accordance with the movement as shown in A of FIG. 30, for example.

In the past, a position of a viewpoint is estimated from an eye pupil of an image, but this method is difficult to do so with high accuracy. Then, the distance measuring method described in the first embodiment is used to measure a distance to eyeballs (irises) of the user (object 121) and a position and inclination of a plane of the irises and estimate the viewpoint.

Human eyes have convergence, so that when the eyes view a near object as shown in C of FIG. 30, they approach each other and each eyeball rotates in a different direction. On this occasion, the plane of the irises is inclined as the eyeballs rotate. A line of sight is oriented substantially perpendicular to the plane of the irises as shown in C of FIG. 30 and passes through the center of a pupil as shown in B of FIG. 30. Therefore, the line of sight can be uniquely determined from the inclination of the irises, the distance to the irises and the position of the irises. Further, the viewpoint can be obtained from the line of sight of both the eyes.

Figure 31:
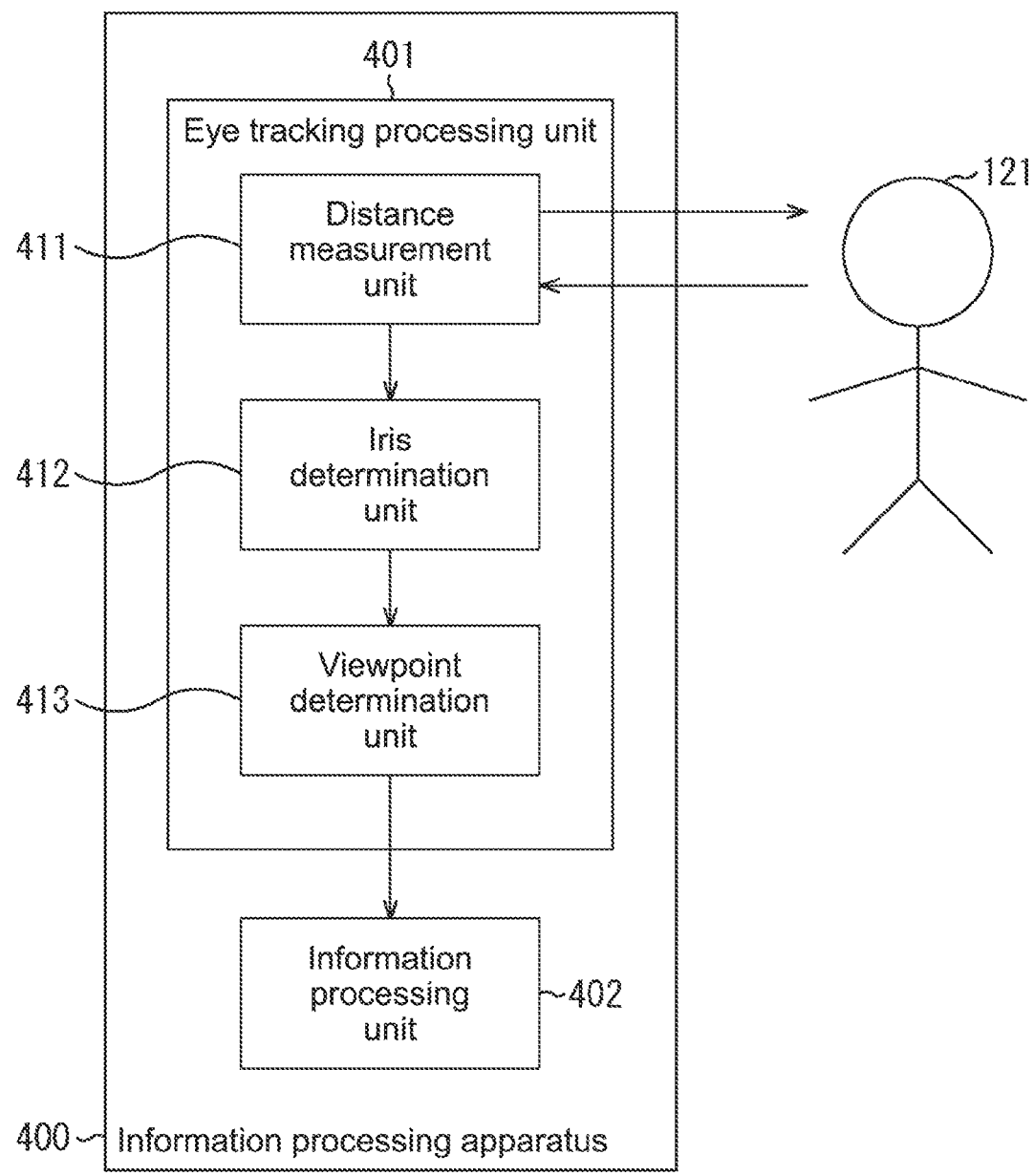
FIG. 31 is a block diagram showing a main configuration example of an information processing apparatus performing the eye tracking.

FIG. 31 is a block diagram showing a main configuration example of the information processing apparatus according to an embodiment of the information processing apparatus to which the present technology is applied. The information processing apparatus 400 shown in FIG. 31 can perform the eye tracking processing as described above.

As shown in FIG. 31, the information processing apparatus 400 includes an eye tracking processing unit 401 and an information processing unit 402. The eye tracking processing unit 401 performs the eye tracking processing to which the present technology is applied and supplies information representing the user's viewpoint to the information processing unit 402 as the processing result. Based on the supplied information, the information processing unit 402 performs predetermined processing in accordance with the user's viewpoint or its movement.

The eye tracking processing unit 401 includes a distance measurement unit 411, an iris determination unit 412, and a viewpoint determination unit 413.

The distance measurement unit 411 has the same configuration as that of the distance measuring apparatus 100 in FIG. 1 and measures the distance with use of the astigmatism as described in the first embodiment. The distance measurement unit 411 supplies the measurement result (that is, distance information) to the iris determination unit 412.

The iris determination unit 412 is constituted of, for example, the CPU, the ROM, the RAM and the like, and performs processing regarding determination of the distance to the irises and the position and the inclination of the irises. The viewpoint determination unit 413 is constituted of, for example, the CPU, the ROM, the RAM and the like, and performs processing regarding determination of the user's viewpoint.

Figure 32:
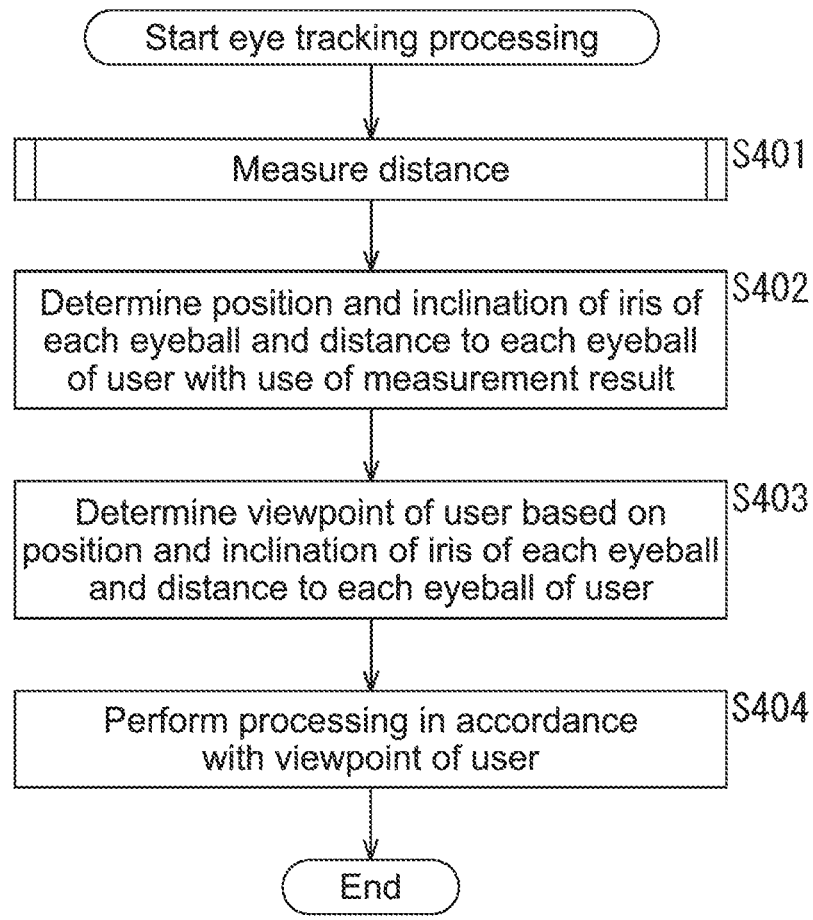
FIG. 32 is a block diagram showing an example of the state of eye tracking processing.

When performing the eye tracking processing, the information processing apparatus 400 executes the eye tracking processing. Referring to a flowchart in FIG. 32, an example of a flow of this eye tracking processing will be described.

When the eye tracking processing is started, in step S401, as described by referring to the flowchart in FIG. 26, the distance measurement unit 411 of the information processing apparatus 400 executes the distance measuring processing and measures the distance to the iris of the user (object 121) in detail. The distance measurement unit 411 supplies the measurement result to the iris determination unit 412.

In step S402, the iris determination unit 412 uses the measurement result obtained by the processing in step S401 to determine the position and the inclination of the iris of each eyeball and the distance to each eyeball of the user (object 121). The iris determination unit 412 supplies the determination result to the viewpoint determination unit 413.

In step S403, the viewpoint determination unit 413 determines the viewpoint of the user (object 121) based on the position and the inclination of the iris of each eyeball and the distance to each eyeball of the user supplied from the iris determination unit 412. The viewpoint determination unit 413 supplies the determination result to the information processing unit 402.

In step S404, the information processing unit 402 performs processing in accordance with the viewpoint of the user obtained by the processing in step S403.

When the processing in step S404 is completed, the eye tracking processing is completed. It should be noted that the eye tracking processing may be executed continuously and repetitively.

As described above, by using the present technology (the distance measuring method described in the first embodiment) to perform the eye tracking processing, the information processing apparatus 400 can more readily and precisely perform the eye tracking processing.

4. Fourth Embodiment

Reception of Instruction Input by Gesture

The distance measuring method described in the first embodiment can be used for reception processing of an instruction input by a gesture.

That is, the distance measuring method described in the first embodiment may be used to determine the gesture (attitude and movement) of the user (object 121) and receive the instruction input by the gesture.

Figure 33:
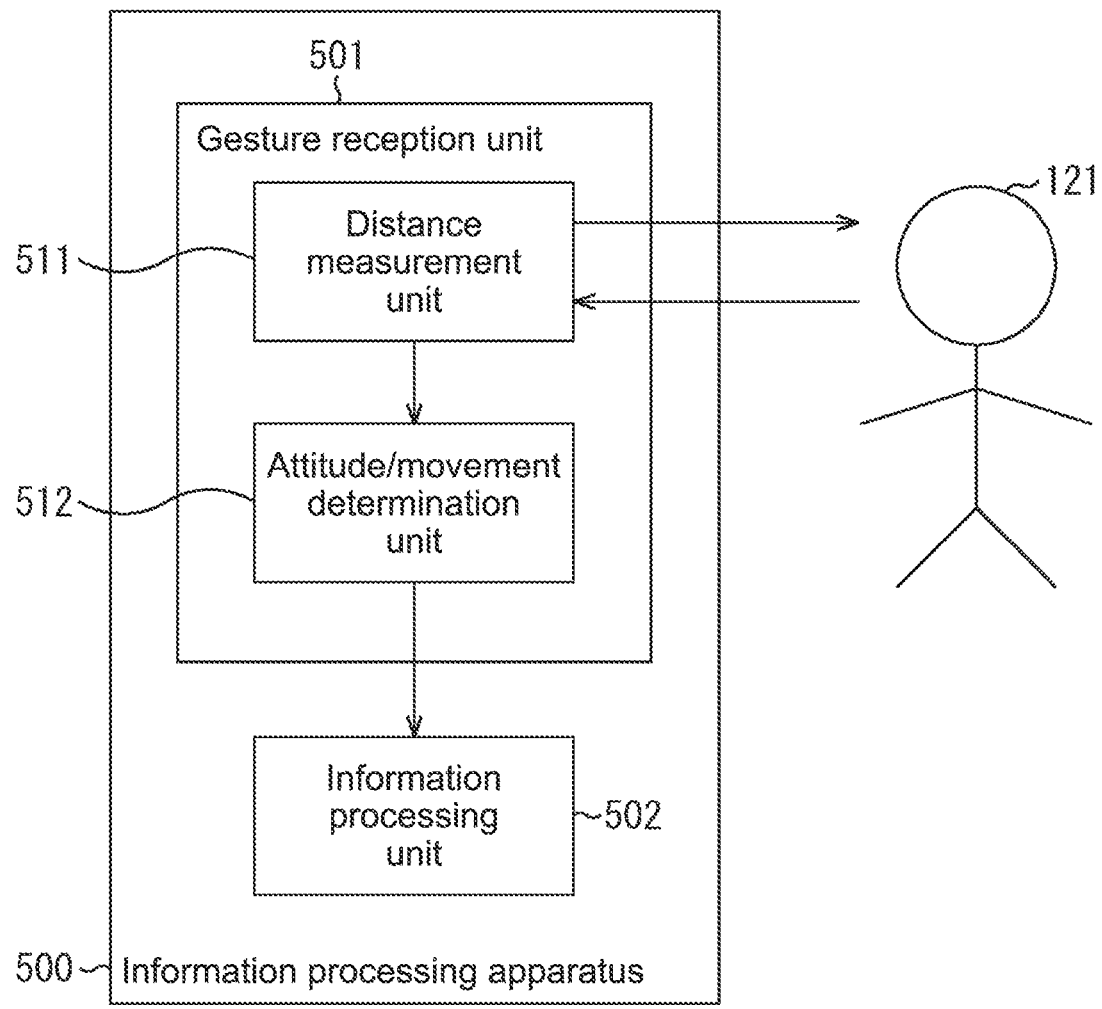
FIG. 33 is a block diagram showing a main configuration example of the information processing apparatus detecting a user's gesture.

FIG. 33 is a block diagram showing a main configuration example of the information processing apparatus according to an embodiment of the information processing apparatus to which the present technology is applied. An information processing apparatus 500 shown in FIG. 33 is an apparatus for receiving the instruction input by the gesture as described above and performing processing in accordance with the instruction.

As shown in FIG. 33, the information processing apparatus 500 includes a gesture reception unit 501 and an information processing unit 502. The gesture reception unit 501 uses the distance measuring method to which the present technology is applied and performs processing regarding reception of the instruction input by the gesture (attitude and movement) of the user (object 121). The information processing unit 502 executes predetermined processing in accordance with the gesture of the user received by the gesture reception unit 501.

The gesture reception unit 501 includes a distance measurement unit 511 and an attitude/movement determination unit 512.

The distance measurement unit 511 has the same configuration as that of the distance measuring apparatus 100 in FIG. 1 and measures the distance with use of the astigmatism as described in the first embodiment. The distance measurement unit 511 supplies the measurement result (that is, distance information) to the attitude/movement determination unit 512.

The attitude/movement determination unit 512, constituted of, for example, the CPU, the ROM, the RAM and the like, uses the measurement result obtained in the distance measurement unit 511 to perform processing regarding determination of the attitude and the movement of the user (object 121).

Figure 34:
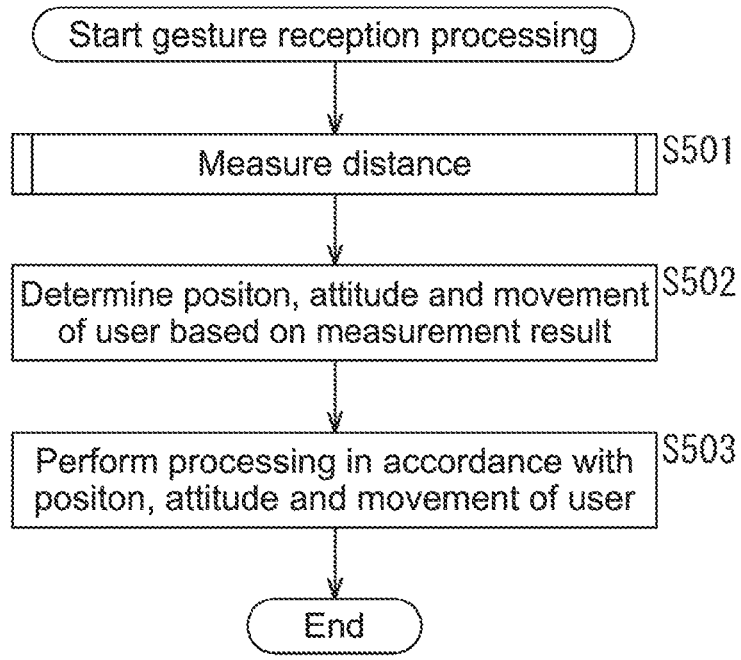
FIG. 34 is a flowchart describing an example of a flow of gesture reception processing.

When receiving the instruction input by the gesture, the information processing apparatus 500 executes the gesture reception processing. Referring to a flowchart in FIG. 34, an example of a flow of this gesture reception processing will be described.

When the gesture reception processing is started, in step S501, as described by referring to the flowchart in FIG. 26, the distance measurement unit 511 of the information processing apparatus 500 executes the distance measuring processing and measures, in detail, the distance to the user (object 121) performing the gesture. The distance measurement unit 511 supplies the measurement result to the attitude/movement determination unit 512.

In step S502, the attitude/movement determination unit 512 uses the measurement result obtained by the processing in step S501 to determine the position, the attitude and the movement of the user (object 121). For example, the attitude/movement determination unit 512 determines the position and the attitude of the user (object 121) at a certain time from a measurement result at the certain time. Moreover, for example, the attitude/movement determination unit 512 determines the movement of the user (object 121) from a measurement result at a plurality of times (or from the determination result of the position and the attitude of the user at the plurality of times). The attitude/movement determination unit 512 supplies the determination result to the information processing unit 502.

In step S503, the information processing unit 502 performs processing in accordance with the position, the attitude and the movement of the user obtained by the processing in step S502.

When the processing in step S503 is completed, the gesture reception processing is completed. It should be noted that the gesture reception processing may be executed continuously and repetitively.

As described above, by using the present technology (the distance measuring method described in the first embodiment) to perform the gesture reception processing, the information processing apparatus 500 can more readily and precisely receive the instruction input by the gesture.

5. Fifth Embodiment

Automatic Focusing

The distance measuring method described in the first embodiment can be used for automatic focusing of an imaging apparatus and other apparatus.

The automatic focusing of the related art includes a light radiation system and an image plane phase difference system. The light radiation system is a system for detecting a distance by a radiation angle, but in this case, it is difficult to increase accuracy sufficiently. Moreover, the image plane phase difference system is a system for splitting light into two portions to guide them to a dedicated sensor and deciding a direction and an amount of a focus from an interval of two images formed. However, this system needs to form a dedicated pixel separately.

Figure 35:
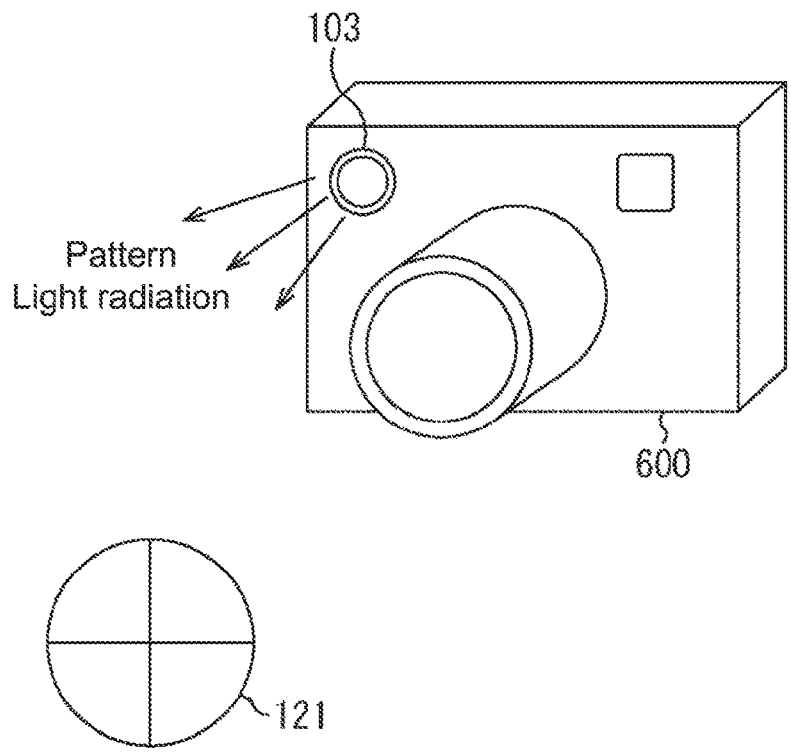
FIG. 35 is a diagram describing an example of a state of an autofocus adjustment of an imaging apparatus.

Then, it may be configured to use the distance measuring method described in the first embodiment to measure a distance by recognizing the pattern as shown in the example of FIG. 35 and use the measurement result to perform automatic focusing.

Figure 36:
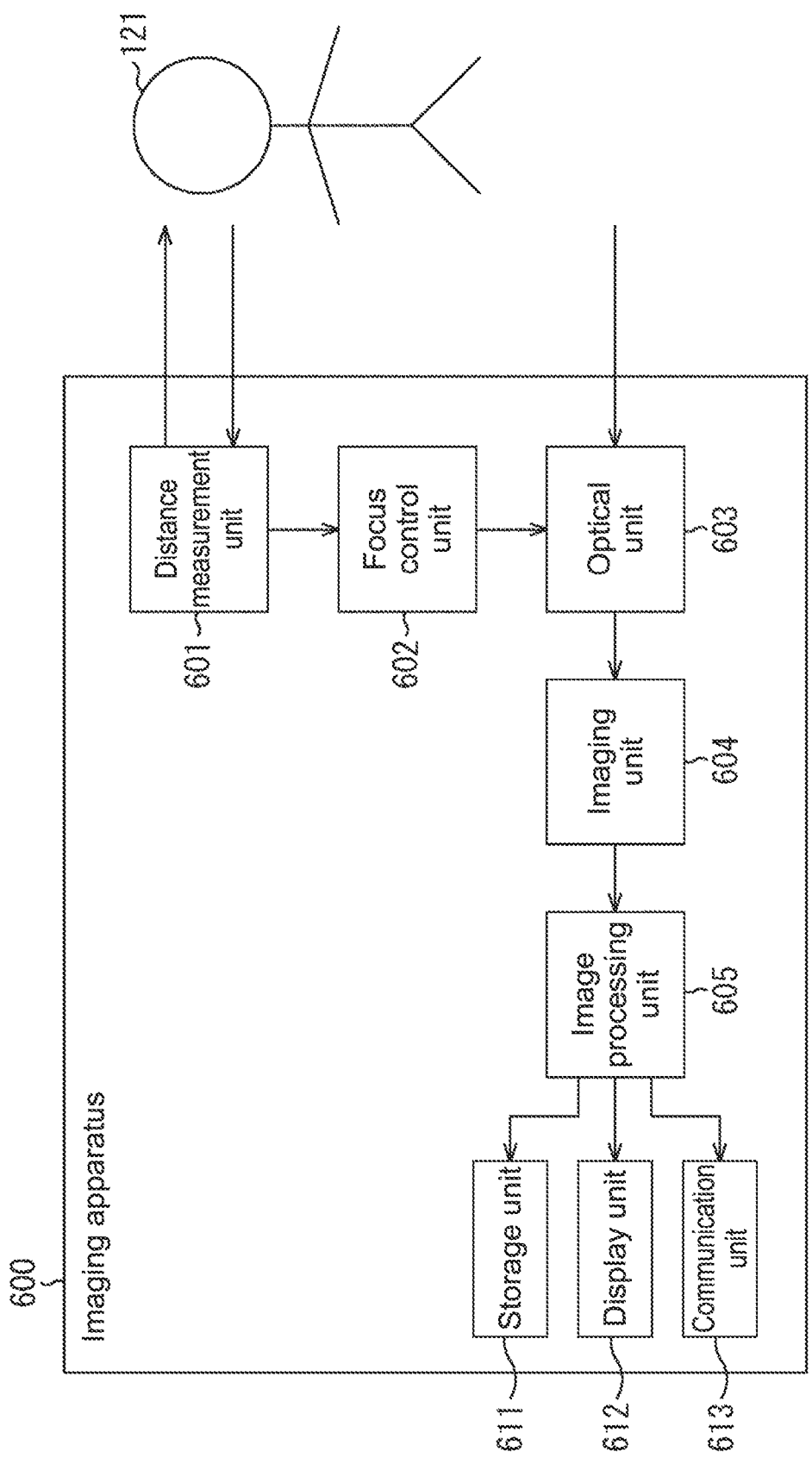
FIG. 36 is a block diagram showing a main configuration example of the imaging apparatus.

FIG. 36 is a block diagram showing a main configuration example of the imaging apparatus according to an embodiment of the information processing apparatus to which the present technology is applied. An imaging apparatus 600 shown in FIG. 36 is an apparatus for imaging a subject (object 121) and obtaining a captured image. The imaging apparatus 600 uses the distance measuring method described in the first embodiment to measure the distance to the subject (object 121) and adjust a focal length based on the measurement result.

As shown in FIG. 36, the imaging apparatus 600 includes a distance measurement unit 601, a focus control unit 602, an optical unit 603, an imaging unit 604, an image processing unit 605, a storage unit 611, a display unit 612, and a communication unit 613.

The distance measurement unit 601 has the same configuration as that of the distance measuring apparatus 100 in FIG. 1 and measures the distance to the subject (object 121) with use of the astigmatism as described in the first embodiment. The distance measurement unit 601 supplies the measurement result (that is, distance information) to the focus control unit 602.

The focus control unit 602, constituted of, for example, the CPU, the ROM, the RAM, an actuator and the like, controls the optical unit 603 and adjusts the focal length of the image (performs automatic focusing) based on the distance to the subject (object 121) supplied from the distance measurement unit 601. For example, the focus control unit 602 controls the optical unit 603 to focus on the subject (object 121) and controls the focal length of the image.

The optical unit 603 is constituted of an optical element such as a lens and a diaphragm and is controlled by the focus control unit 602 and can change the focal length. The optical unit 603 induces an optical influence to light from the subject entering the imaging unit 604 at the time of imaging.

The imaging unit 604 includes an image sensor such as a CCD and a CMOS, uses the image sensor to photoelectrically convert the light from the subject entered through the optical unit 603, and obtains an image data of the captured image. The imaging unit 604 supplies the obtained image data to the image processing unit 605.

The image processing unit 605, constituted of, for example, the CPU, the ROM, the RAM and the like, performs predetermined image processing to the image data supplied from the imaging unit 604. The image processing unit 605 supplies the image data after image processing to the storage unit 611 so that the image data is stored into the storage unit 611, supplies the image data to the display unit 612 so that the image data is displayed on a monitor as an image, and supplies the image data to the communication unit 613 so that the image data is transferred to other apparatus.

The storage unit 611 includes a storage medium such as a flash memory and a hard disk and stores the image data supplied from the image processing unit 605 into the storage medium.

The display unit 612 includes a monitor such as an LCD and displays the image of the image data supplied from the image processing unit 605.

The communication unit 613 includes a wire or a wireless communication interface and transfers the image data supplied from the image processing unit 605 to other apparatus through a communication medium.

Figure 37:
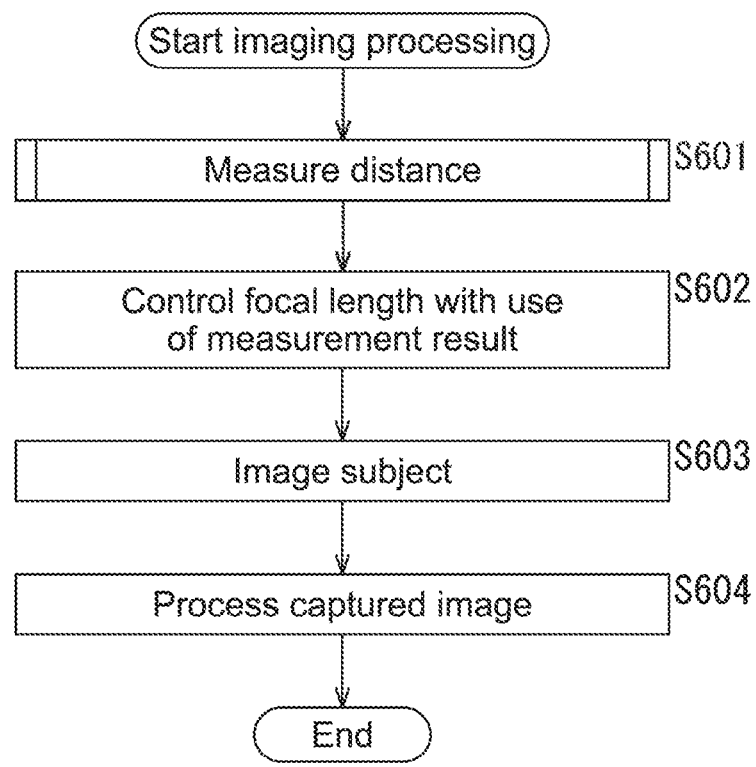
FIG. 37 is a flowchart describing an example of a flow of imaging processing.

When imaging the subject, the imaging apparatus 600 executes imaging processing. Referring to a flowchart in FIG. 37, an example of a flow of this imaging processing will be described.

When the imaging processing is started, in step S601, as described by referring to the flowchart in FIG. 26, the distance measurement unit 601 of the imaging apparatus 600 executes the distance measuring processing and measures the distance to the subject (object 121). The distance measurement unit 601 supplies the measurement result to the focus control unit 602.

In step S602, the focus control unit 602 uses the measurement result obtained by the processing in step S601 to control the focal length of the optical unit 603. For example, the focus control unit 602 control the optical unit 603 to focus the focal length to the subject (object 121).

In step S603, the imaging unit 604 images the subject (object 121) based on the instruction from the user and the like.

In step S604, the image processing unit 605 perform predetermined image processing to the image data of the captured image obtained by the imaging in step S603. The image data that has been subjected to image processing is supplied to the storage unit 611 so that the image data is stored into the storage medium, to the display unit 612 so that the image data is displayed on the monitor, and to the communication unit 613 so that the image data is transferred to other apparatus.

When the processing in step S604 is completed, the image processing is completed.

As described above, by using the present technology (the distance measuring method described in the first embodiment) to perform the automatic focusing, the imaging apparatus 600 can perform the automatic focusing more accurately, without forming the dedicated pixel.

6. Sixth Embodiment

Computer

The series of processing described above can be executed by hardware but can also be executed by software. When the series of processing is executed by software, a program that configures such software is installed into a computer. Here, the computer includes a computer in which dedicated hardware is incorporated and a general-purpose personal computer or the like that is capable of executing various functions when various programs are installed.

Figure 38:
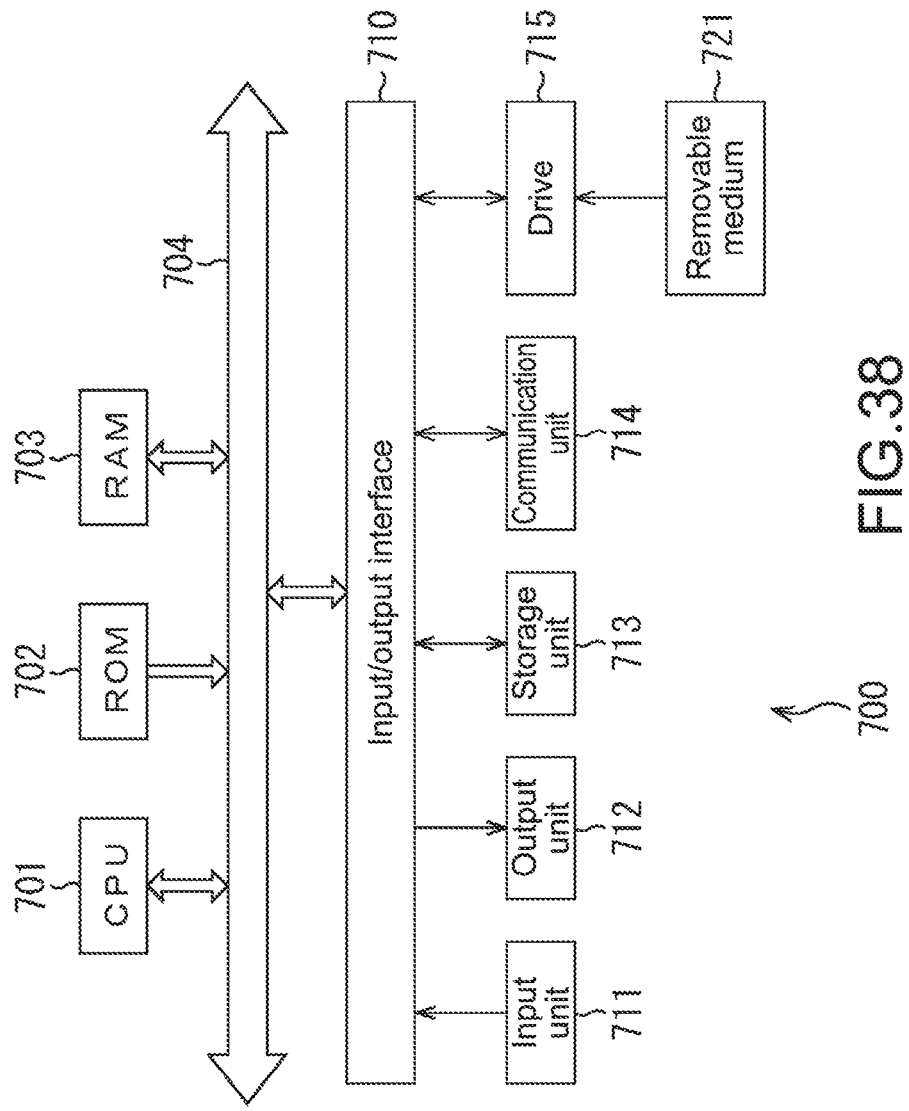
FIG. 38 is a block diagram showing a main configuration example of a computer.

FIG. 38 is a block diagram showing an example configuration of the hardware of a computer that executes the series of processing described above according to a program.

In a computer 700 shown in FIG. 38, a central processing unit (CPU) 701, a read only memory (ROM) 702 and a random access memory (RAM) 703 are mutually connected by a bus 704.

An input/output interface 710 is also connected to the bus 704. An input unit 711, an output unit 712, a storage unit 713, a communication unit 714, and a drive 715 are connected to the input/output interface 710.

The input unit 711 is configured from a keyboard, a mouse, a microphone, a touch panel, an input terminal, and the like. The output unit 712 is configured from a display, a speaker, an input terminal, and the like. The storage unit 713 is configured from a hard disk, a RAM disk, a non-volatile memory, and the like. The communication unit 714 is configured from a network interface and the like. The drive 715 drives a removable medium 721 such as a magnetic disk, an optical disk, a magneto-optical disk, and a semiconductor memory.

In the computer configured as described above, the CPU 701 loads a program that is stored, for example, in the storage unit 713 onto the RAM 703 through the input/output interface 710 and the bus 704, and executes the program. Therefore, the above-described series of processing is performed. The RAM 703 stores data in a suitable manner, which is necessary for the CPU 701 to execute various processing.

A program executed by the computer (CPU 701) may be recorded in the removable medium 721 as a package medium or the like, for example, and may be applied. In that case, by mounting the removable medium 721 on the drive 715, the program can be installed into the storage unit 713 through the input/output interface 710.

Moreover, the program may be provided through a wired or wireless transmission medium, such as a local area network, the Internet or digital satellite broadcasting. In that case, the communication unit 714 may receive the program, and the program may be installed in the storage 713.

As another alternative, the program can be installed in advance into the ROM 702 or the storage unit 713.

It should be noted that the program executed by a computer may be a program that is processed in time series according to the sequence described in this specification or a program that is processed in parallel or at necessary timing such as upon calling.

Moreover, in this specification, the steps describing the program stored in the recording medium include not only processing performed in time series according to the sequence shown therein but also processing executed in parallel or individually, not necessarily performed in time series.

Moreover, in the present specification, a system has the meaning of a set of a plurality of configured elements (such as an apparatus or a module (part)), and does not take into account whether or not all the configured elements are in the same casing. Therefore, the system may be either a plurality of apparatuses stored in separate casings and connected through a network, or a single apparatus stored in a plurality of modules within a single casing.

Moreover, an element described as a single apparatus (or processing unit) above may be configured to be divided as a plurality of apparatuses (or processing units). On the contrary, elements described as a plurality of apparatuses (or processing units) above may be configured collectively as a single apparatus (or processing unit). Moreover, an element other than those described above may be added to each apparatus (or processing unit). Further, a part of an element of a given apparatus (or processing unit) may be included in an element of another apparatus (or another processing unit) as long as the configuration or operation of the system as a whole is substantially the same.

The suitable embodiments of the present disclosure have been described above in detail with reference to the attached drawings. The technical scope of the present disclosure is not limited to those examples. It should be understood by those skilled in the art that various modifications, combinations, sub-combinations and alterations may occur depending on design requirements and other factors insofar as they are within the scope of the appended claims or the equivalents thereof.

For example, the present technology may employ a configuration of cloud computing, in which a plurality of apparatuses share one function and process the function together through a network.

Moreover, one apparatus may execute the steps described with reference to the flowcharts, or a plurality of apparatuses may share and execute the steps.

Further, in a case where one step includes a plurality of processing, one apparatus may execute the plurality of processing in the step, or a plurality of apparatuses may share and execute the plurality of processing.

It should be noted that the present technology may also be configured as follows.

(1) An information processing apparatus, including:
a light emitting unit configured to emit light; an optical unit configured to induce an optical influence to the light from the light emitting unit, the optical unit having an astigmatic lens configured to generate astigmatism with a plurality of focal lengths;
a detecting unit configured to detect the light emitted in the light emitting unit, radiated outside through the optical unit, and reflected by an object; and
a measuring unit configured to measure a distance to the object based on astigmatism generated in the reflection light detected in the detecting unit.

(2) The information processing apparatus according to any one of Items (1) and (3) to (19), in which the measuring unit is configured to measure the distance to the object based on a change in a radiation shape of the light in the object.

(3) The information processing apparatus according to any one of Items (1), (2) and (4) to (19), in which
the measuring unit is configured to measure the distance to the object in accordance with a change in a thickness of each line, in the object, of the light linearly radiated in a plurality of directions.

(4) The information processing apparatus according to any one of Items (1) to (3) and (5) to (19), in which
the optical unit further includes one of a slit, a waveguide, and a diffractive optical element configured to form the radiation shape of the light from the light emitting unit into a cross-shape, and
the measuring unit is configured to measure the distance to the object in accordance with a change in a thickness of each line of the cross-shape in the object.

(5) The information processing apparatus according to any one of Items (1) to (4) and (6) to (19), in which
the optical unit further includes one of a slit, a waveguide, and a diffractive optical element configured to form the radiation shape of the light from the light emitting unit into a radial shape, and
the measuring unit is configured to measure the distance to the object in accordance with a change in a thickness of each line of the radial shape in the object.

(6) The information processing apparatus according to any one of Items (1) to (5) and (7) to (19), in which
the optical unit further includes one of a slit, a waveguide, and a diffractive optical element configured to radiate the light from the light emitting unit to a plurality of positions, and
the measuring unit is configured to measure the distance to the object in accordance with a change in the radiation shape of the light radiated to the plurality of positions of the object.

(7) The information processing apparatus according to any one of Items (1) to (6) and (8) to (19), in which
the optical unit further includes one of a slit, a waveguide, and a diffractive optical element configured to form the radiation shape of the light from the light emitting unit into a stripe shape, and
the measuring unit is configured to measure the distance to the object in accordance with a change in a thickness of each line of the stripe shape in the object.

(8) The information processing apparatus according to any one of Items (1) to (7) and (9) to (19), in which
the astigmatic lens is a lens configured such that the focal lengths do not change in a radial direction (sagittal) from a central side of the astigmatic lens toward a peripheral side and the focal lengths continuously change in a concentric direction (meridional) centered at one of the center of the astigmatic lens and a vicinity of the center.

(9) The information processing apparatus according to any one of Items (1) to (8) and (10) to (19), in which the astigmatic lens is a convertible lens having the focal lengths variable.

(10) The information processing apparatus according to any one of Items (1) to (9) and (11) to (19), in which
the convertible lens is a lenticular lens.

(11) The information processing apparatus according to any one of Items (1) to (10) and (12) to (19), in which
the astigmatic lens is constituted of a plurality of lenses.

(12) The information processing apparatus according to any one of Items (1) to (11) and (13) to (19), in which
the measuring unit is configured to further measure the distance to the object based on displacement of the reflection light detected in the detecting unit and to measure the distance to the object with use of both a measurement result based on the displacement and a distance measurement result based on the astigmatism.

(13) The information processing apparatus according to any one of Items (1) to (12) and (14) to (19), in which
the light emitting unit is configured to emit infrared light, and
the detecting unit is configured to detect reflection light of the infrared light radiated outside through the optical unit and reflected by the object.

(14) The information processing apparatus according to any one of Items (1) to (13) and (15) to (19), in which
the detecting unit includes an imaging element capable of detecting received visible light and the infrared light and is configured to obtain a captured image made of the visible light with use of the imaging element and detect the reflection light of the infrared light.

(15) The information processing apparatus according to any one of Items (1) to (14) and (16) to (19), in which
the light emitting unit is configured to emit laser light, and
the detecting unit is configured to detect reflection light of the laser light radiated outside through the optical unit and reflected by the object.

(16) The information processing apparatus according to any one of Items (1) to (15) and (17) to (19), further including:
a recognition unit configured to recognize a three-dimensional shape of iris wrinkles of eyeballs of a person serving as the object with use of the distance to the object that is measured by the measuring unit; and
an authentication unit configured to authenticate the person based on the three-dimensional shape of the iris wrinkles that is recognized by the recognition unit.

(17) The information processing apparatus according to any one of Items (1) to (16), (18), and (19), further including:
an iris determination unit configured to determine a position and an inclination of an iris of each eyeball and a distance to the eyeball of a person serving as the object with use of the distance to the object that is measured by the measuring unit;
a viewpoint determination unit configured to determine a viewpoint of the person based on the position and the inclination of the iris of the eyeball and the distance to the eyeball determined by the iris determination unit; and
an information processing unit configured to perform processing in accordance with the viewpoint of the person that is determined by the viewpoint determination unit.

(18) The information processing apparatus according to any one of Items (1) to (17) and (19), further including:
an attitude/movement determination unit configured to determine a position, an attitude and a movement of a person serving as the object with use of the distance to the object that is measured by the measuring unit; and
an information processing unit configured to perform processing in accordance with the position, the attitude and the movement of the person that is determined by the attitude/movement determination unit.

(19) The information processing apparatus according to any one of Items (1) to (18), further including:
an imaging optical unit configured to allow light from a subject to transmit through the imaging optical unit, the imaging optical unit having a variable focal length;
an imaging unit configured to photoelectrically convert the light from the subject that is received through the imaging optical unit and obtain image data of the subject; and
a focus control unit configured to control the focal length of the imaging optical unit with use of the distance to the object that is measured by the measuring unit.

(20) An information processing method, including:
emitting light;
detecting the light that is radiated outside through an optical unit configured to induce an optical influence to the light and is reflected by an object, the optical unit having an astigmatic lens configured to generate astigmatism with a plurality of focal lengths; and
measuring a distance to the object based on the astigmatism generated in the detected reflection light.

It should be understood by those skilled in the art that various modifications, combinations, sub-combinations and alterations may occur depending on design requirements and other factors insofar as they are within the scope of the appended claims or the equivalents thereof.

What is claimed is:

1. An information processing apparatus, comprising:
a light emitting unit configured to emit light;
an optical unit configured to induce an optical influence to the light from the light emitting unit, the optical unit having an astigmatic lens configured to generate astigmatism with a plurality of focal lengths;
a detecting unit configured to detect the light emitted in the light emitting unit, radiated outside through the optical unit, and reflected by an object; and
a measuring unit configured to measure a distance to the object based on astigmatism generated in the reflection light detected in the detecting unit.

2. The information processing apparatus according to claim 1, wherein
the measuring unit is configured to measure the distance to the object based on a change in a radiation shape of the light in the object.

3. The information processing apparatus according to claim 2, wherein
the measuring unit is configured to measure the distance to the object in accordance with a change in a thickness of each line, in the object, of the light linearly radiated in a plurality of directions.

4. The information processing apparatus according to claim 3, wherein
the optical unit further includes one of a slit, a waveguide, and a diffractive optical element configured to form the radiation shape of the light from the light emitting unit into a cross-shape, and
the measuring unit is configured to measure the distance to the object in accordance with a change in a thickness of each line of the cross-shape in the object.

5. The information processing apparatus according to claim 3, wherein
the optical unit further includes one of a slit, a waveguide, and a diffractive optical element configured to form the radiation shape of the light from the light emitting unit into a radial shape, and the measuring unit is configured to measure the distance to the object in accordance with a change in a thickness of each line of the radial shape in the object.

6. The information processing apparatus according to claim 3, wherein
the optical unit further includes one of a slit, a waveguide, and a diffractive optical element configured to radiate the light from the light emitting unit to a plurality of positions, and
the measuring unit is configured to measure the distance to the object in accordance with a change in the radiation shape of the light radiated to the plurality of positions of the object.

7. The information processing apparatus according to claim 3, wherein
the optical unit further includes one of a slit, a waveguide, and a diffractive optical element configured to form the radiation shape of the light from the light emitting unit into a stripe shape, and
the measuring unit is configured to measure the distance to the object in accordance with a change in a thickness of each line of the stripe shape in the object.

8. The information processing apparatus according to claim 1, wherein
the astigmatic lens is a lens configured such that the focal lengths do not change in a radial direction (sagittal) from a central side of the astigmatic lens toward a peripheral side and the focal lengths continuously change in a concentric direction (meridional) centered at one of the center of the astigmatic lens and a vicinity of the center.

9. The information processing apparatus according to claim 1, wherein
the astigmatic lens is a convertible lens having the focal lengths variable.

10. The information processing apparatus according to claim 9, wherein
the convertible lens is a lenticular lens.

11. The information processing apparatus according to claim 1, wherein
the astigmatic lens is constituted of a plurality of lenses.

12. The information processing apparatus according to claim 1, wherein
the measuring unit is configured to further measure the distance to the object based on displacement of the reflection light detected in the detecting unit and to measure the distance to the object with use of both a measurement result based on the displacement and a distance measurement result based on the astigmatism.

13. The information processing apparatus according to claim 1, wherein
the light emitting unit is configured to emit infrared light, and
the detecting unit is configured to detect reflection light of the infrared light radiated outside through the optical unit and reflected by the object.

14. The information processing apparatus according to claim 13, wherein
the detecting unit includes an imaging element capable of detecting received visible light and the infrared light and is configured to obtain a captured image made of the visible light with use of the imaging element and detect the reflection light of the infrared light.

15. The information processing apparatus according to claim 1, wherein
the light emitting unit is configured to emit laser light, and
the detecting unit is configured to detect reflection light of the laser light radiated outside through the optical unit and reflected by the object.

16. The information processing apparatus according to claim 1, further comprising:
a recognition unit configured to recognize a three-dimensional shape of iris wrinkles of eyeballs of a person serving as the object with use of the distance to the object that is measured by the measuring unit; and
an authentication unit configured to authenticate the person based on the three-dimensional shape of the iris wrinkles that is recognized by the recognition unit.

17. The information processing apparatus according to claim 1, further comprising:
an iris determination unit configured to determine a position and an inclination of an iris of each eyeball and a distance to the eyeball of a person serving as the object with use of the distance to the object that is measured by the measuring unit;
a viewpoint determination unit configured to determine a viewpoint of the person based on the position and the inclination of the iris of the eyeball and the distance to the eyeball determined by the iris determination unit; and
an information processing unit configured to perform processing in accordance with the viewpoint of the person that is determined by the viewpoint determination unit.

18. The information processing apparatus according to claim 1, further comprising:
an attitude/movement determination unit configured to determine a position, an attitude and a movement of a person serving as the object with use of the distance to the object that is measured by the measuring unit; and
an information processing unit configured to perform processing in accordance with the position, the attitude and the movement of the person that is determined by the attitude/movement determination unit.

19. The information processing apparatus according to claim 1, further comprising:
an imaging optical unit configured to allow light from a subject to transmit through the imaging optical unit, the imaging optical unit having a variable focal length;
an imaging unit configured to photoelectrically convert the light from the subject that is received through the imaging optical unit and obtain image data of the subject; and
a focus control unit configured to control the focal length of the imaging optical unit with use of the distance to the object that is measured by the measuring unit.

20. An information processing method, comprising:
emitting light;
detecting the light that is radiated outside through an optical unit configured to induce an optical influence to the light and is reflected by an object, the optical unit having an astigmatic lens configured to generate astigmatism with a plurality of focal lengths; and
measuring a distance to the object based on the astigmatism generated in the detected reflection light.

* * * * *